United States Patent
Vournakis et al.

(10) Patent No.: US 7,931,637 B2
(45) Date of Patent: Apr. 26, 2011

(54) HEMOSTATIC COMPOSITIONS AND USES THEREFOR

(75) Inventors: John N. Vournakis, Somerville, MA (US); Sergio Finkielsztein, Newton, MA (US)

(73) Assignee: Marine Polymer Technologies, Inc., Danvers, MA (US)

( * ) Notice: Subject to any disclaimer, the term of this patent is extended or adjusted under 35 U.S.C. 154(b) by 1976 days.

(21) Appl. No.: 10/749,330

(22) Filed: Dec. 31, 2003

(65) Prior Publication Data

US 2004/0237970 A1 Dec. 2, 2004

Related U.S. Application Data

(60) Provisional application No. 60/437,349, filed on Dec. 31, 2002.

(51) Int. Cl.
*A61F 13/15* (2006.01)

(52) U.S. Cl. .................................. 604/389; 604/390

(58) Field of Classification Search .................. 604/57, 604/59, 73, 289–290; 606/213–214
See application file for complete search history.

(56) References Cited

U.S. PATENT DOCUMENTS

| | | |
|---|---|---|
| 4,394,373 A | 7/1983 | Malette et al. |
| 5,437,292 A | 8/1995 | Kipshidze et al. |
| 5,510,102 A | 4/1996 | Cochrum |
| 5,564,849 A | 10/1996 | Greer, Jr. |
| 5,622,834 A | 4/1997 | Vournakis et al. |
| 5,623,064 A | 4/1997 | Vournakis et al. |
| 5,624,679 A | 4/1997 | Vournakis et al. |
| 5,635,493 A | 6/1997 | Vournakis et al. |
| 5,686,115 A | 11/1997 | Vournakis et al. |
| 5,746,755 A | 5/1998 | Wood et al. |
| 5,846,952 A | 12/1998 | Vournakis et al. |
| 5,858,350 A | 1/1999 | Vournakis et al. |
| 6,056,970 A | 5/2000 | Greenawalt et al. |
| 6,063,911 A | 5/2000 | Vournakis et al. |
| 6,162,241 A | 12/2000 | Coury et al. |
| 6,193,670 B1 | 2/2001 | Van Tassel et al. |
| 6,361,551 B1 | 3/2002 | Torgerson et al. |
| 6,599,720 B2 | 7/2003 | Vournakis et al. |
| 6,610,668 B2 | 8/2003 | Vournakis et al. |
| 6,630,459 B2 | 10/2003 | Vournakis et al. |
| 6,649,599 B2 | 11/2003 | Vournakis et al. |
| 6,743,783 B1 | 6/2004 | Vournakis et al. |
| 2002/0006429 A1 | 1/2002 | Redmond et al. |

(Continued)

FOREIGN PATENT DOCUMENTS

JP 2001-513368 9/2001

(Continued)

OTHER PUBLICATIONS

U.S. Appl. No. 60/437,349, filed Dec. 31, 2002, Vournakis et al.

(Continued)

*Primary Examiner* — Michele Kidwell
(74) *Attorney, Agent, or Firm* — Jones Day

(57) ABSTRACT

The present invention relates generally to the field of hemostasis, including methods, compositions, and devices that can be employed to achieve hemostasis at an increased rate. More specifically the present invention relates to hemostatic compositions that achieve a hemostatic effect at a distance from the site of application of the composition, and a method for administering such a composition to effectively reduce localized vascular complications associated with treating a breach or puncture in a vein or artery and reduce the time to achieve hemostasis.

33 Claims, 1 Drawing Sheet

U.S. PATENT DOCUMENTS

Figure 1:
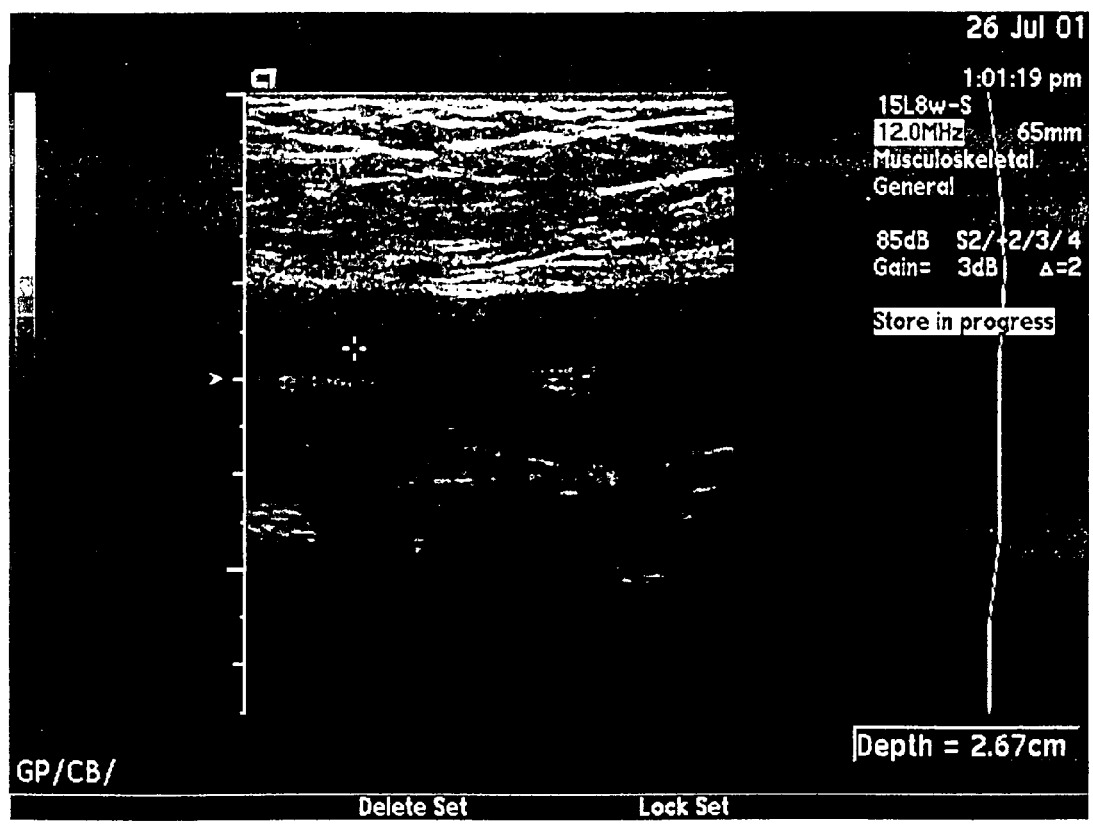

| | | | |
|---|---|---|---|
| 2002/0197302 A1 | 12/2002 | Cochrum et al. | |
| 2003/0078234 A1 | 4/2003 | Vournakis et al. | |
| 2003/0129183 A1* | 7/2003 | Spillert et al. | 424/94.64 |
| 2004/0087015 A1 | 5/2004 | Vournakis et al. | |

FOREIGN PATENT DOCUMENTS

| | | |
|---|---|---|
| WO | WO 95/15343 | 6/1995 |
| WO | WO 99/07417 | 2/1999 |
| WO | WO 00/36918 | 6/2000 |
| WO | WO 02/063961 | 8/2002 |
| WO | WO 2004/060172 | 7/2004 |
| WO | WO 2004/076637 | 9/2004 |

OTHER PUBLICATIONS

Camenzind et al., 1994, "Collagen application versus manual compression: a prospective randomized trial for arterial puncture site closure after coronary angioplasty," J. Am. Coll. Cardiol. 24(3):655-662.

Falstrom et al., 1997, "Reduction of femoral artery bleeding post catheterization using a collagen enhanced fibrin sealant," Cathet. Cardiovasc. Diagn. 41(1):79-84.

Gwechenberger et al., 1997, "Use of a collagen plug versus manual compression for sealing arterial puncture site after cardiac catheterization," Angiology 48(2):121-126.

Hoekstra et al., 1998, "Percutaneous microcrystalline chitosan application for sealing arterial puncture sites," Biomaterials 19(16):1467-1471.

Ismail et al., 1995, "Reduction of femoral arterial bleeding post catheterization using percutaneous application of fibrin sealant," Cathet. Cardiovasc. Diagn. 34(1):88-95.

Kipshidze et al., 1998, "Percutaneous Application of Fibrin Sealant to Achieve Hemostasis Following Arterial Catheterization," J. Invasive Cardiol. 10(3):133-141.

Merino et al., 1992, "Percutaneous vascular hemostasis device for interventional procedures," Cathet. Cardiovasc. Diagn. 26(4):319-322.

Olade et al., 2002, Emedicine Journal 3(3):1-13.

Prior et al., 2000, "Efficacy of a novel hemostatic agent in animal models of impaired hemostasis," J. Biomed. Mater. Res. 53(3):252-257.

Sanborn et al., 1993, "A multicenter randomized trial comparing a percutaneous collagen hemostasis device with conventional manual compression after diagnostic angiography and angioplasty," J. Am. Coll. Cardiol. 22(5):1273-1279.

Silber et al., 1998, "Usefulness of collagen plugging with VasoSeal after PTCA as compared to manual compression with identical sheath dwell times," Cathet. Cardiovasc. Diagn. 43(4):421-427.

Meyer K.B. et al., 1999, "Control of post dialysis bleeding in patients on chronic oral anticoagulation therapy," J Am Soc Nephrol 10:212A, Abtract A1078.

Nader R.G. et al., 2002, "Clinical evaluation of the SyvekPatch® in consecutive patients undergoing interventional, EPS and diagnostic cardiac catheterization procedures," J Invas Cardiol 14(6):305-307.

Najjar S.F. et al., 2004, "Evaluation of poly-N-acetyl glucosamine as a hemostatic agent in patients undergoing cardiac catheterization: a double-blind, randomized study," J Trauma 57:S38-S41.

Roeder B.A.et al., 2002, "Self-sealing, large bore arterial punctures: a counterintuitive new phenomenon," J. Biomech. Eng. 124(4):342-346.

Schrader R. et al., 1992, "Collagen application for sealing of arterial punture sites in comparison to pressare dressing: A randomized trial," Catheteriz. and Cardiovasc. Diagnosis 27(4):298-302.

Shubrooks S.J. et al., 2000, "Earlier ambulation at 2 hours following cardiac catheterization using Syvek Patch®," SCA&I 2000 Meeting Abstracts 143, Abstract PO22.

Smith T.P., et al., 2001, "Infectious complications resulting from use of hemostatic puncture closure devices," A. J. Surg. 182(6):658-62.

Vournakis J.N. et al., 2003, "The RDH bandage: Hemostasis and Survival in a lethal aortotomy hemorrhage model," J. Surg. Res. 113:1-5.

Yanagisawa M. et al., 1988, "A novel potent vasoconstrictor peptide produced by vascular endothelial cells," 332:411-415.

Saishin Igaku Daijiten (Current Medical Dictionary), 2001, p. 24 and p. 687, in Japanese with translation of relevant paragraphs.

Written Opinion for Intern. Appl. No. PCT/US03/41762, mailed Sep. 9, 2004 by International Preliminary Examining Authority.

Inernational Preliminary Report on Patentability for Intern. Appl. No. PCT/US03/41762, mailed Mar. 16, 2009 by International Preliminary Examining Authority.

* cited by examiner

HEMOSTATIC COMPOSITIONS AND USES THEREFOR

This application claims priority of U.S. provisional patent application Ser. No. 60/437,349, filed Dec. 31, 2002, which is incorporated herein by reference in its entirety.

1. FIELD OF THE INVENTION

The present invention relates generally to the field of hemostasis, including methods, compositions, and devices that can be employed to achieve hemostasis at an increased rate or in a reduced period of time. More specifically the present invention relates to hemostatic compositions that achieve a hemostatic effect at a distance from the site of application of the composition, and a method for administering such a composition to effectively reduce localized vascular complications associated with treating a breach or puncture in a vein or artery. The hemostatic compositions can comprise one or more vasoconstrictors or one or more coagulants, or a combination of one or more vasoconstrictors with one or more coagulants. The hemostatic compositions can also comprise a compound that has both vasoconstrictive properties and coagulant properties. The hemostatic compositions can be applied in conjunction with a barrier-forming material to more effectively achieve hemostasis and reduce the occurrence of localized vascular complications.

2. BACKGROUND

Localized vascular complications associated with catheterization of a vein or artery are common side effects with many medical procedures. Such complications including hemorrhaging of blood vessels, delayed hemostasis time, hematoma, pseudoaneurysm, and arteriovenous (AV) fistula formation can be life threatening. Since cardiac catheterization remains the primary technique for diagnosing coronary artery disease and is used to help delineate coronary anatomy, the information gained is often a medical necessity, despite the risks. Traditionally, the application of pressure to a vein or artery effected by a breach or puncture was the preferred method for reducing complications, however compression of a vein or artery after cardiac catheterization can be very painful for the patients. Compression bandages with weights may be applied for 4-8 hours following hemostasis and patients can be immobilized up to 24 hours. Patients frequently develop back pain and urinary retention in addition to the localized vascular complications.

Two approaches have recently been used to reduce localized vascular complications, namely percutaneous closure/sealant devices and hemostatic patches.

Numerous hemostatic patches have been invented to treat superficial wounds on skin or on the surface of internal organs. These patches are effective at the site where the patch contacts the skin or contacts the surface of an internal organ. Application of the patches in treatment of cardiac catheterization presents a problem in that the underlying puncture in the artery or vein is not directly effected by the active components of the patches. Thus, the vein or artery puncture may continue to bleed after the skin puncture wound is sealed and the possibility of hematoma formation or other localized vascular complications exists. U.S. Pat. No. 6,056,970 discloses a hemostatic biocompatable composition and a method of application wherein the composition is topically maintained in contact with the wound on the skin surface, preferably with light pressure, for a period of time for clotting to occur at the interface between the composition and the wound. A related composition is disclosed in U.S. Pat. No. 6,361,551, where a wound-contacting fabric accelerates clot formation at an interface between a wound surface and the hemostatic fabric. The hemostatic fabric is composed of collagen fibers and can comprise numerous hemostatic agents. U.S. Pat. No. 5,564,849 also discloses a similar patch that accelerates clot formation at an interface between a skin or organ wound surface and the hemostatic patch. The patch comprises active amounts of thrombin and epsilon aminocaproic acid (EACA).

Several compositions that can act as hemostatic agents and typically include collagen or fibrin are known (Falstrom et al., 1997, Catheterization and Cardiovasular Diagnosis 41:79-84; Hoekstra et al., 1998, Biomaterials. 19:1467-1471; Prior et al., 2000, Journal of Biomaterials Research. 53(3): 252-257). The main disadvantage of such compositions is their limited use in treating breaches or punctures in veins or arteries at a distance. In order to treat breaches or punctures in veins or arteries at a distance beneath the skin surface with such compositions, it is necessary to apply the compositions in an invasive manner so that the compositions are in contact with a breach or puncture in a vein or artery. Since such compositions are effective at the site of contact, topical treatment at a breach or puncture in a vein or artery that is found at some distance from the skin surface is not possible. U.S. Pat. No. 4,394,373 discloses compositions that act as coagulants and may be used to promote clotting of a wound by placing the compositions in contact with the wound where the composition comprises liquid or powder chitosan. U.S. Pat. No. 5,510,102 discloses compositions that act as coagulants and may be used to promote clotting of a wound by placing the compositions in contact with the wound where the composition comprises platelet rich plasma plus a biocompatable polymer that is a hemostatic agent such as alginate. The compositions of U.S. Pat. Nos. 4,394,373 and 5,510,102 are either applied directly to the wound surface, in the case of treatment of a superficial wound or in the case of a puncture in an artery left by a catheterization procedure, the compositions are typically injected into the soft tissue surrounding the arterial puncture site, so that the composition is in contact with the puncture site. The injection of the compositions is an invasive procedure that can lead to complications such as swelling, further damage to blood vessels and tissue, and increased risk of infection.

Hemostatic patches are effective at the interface of the wound and the patch. Thus, in the case of a puncture in a vein or artery caused by catheterization, when a patch causes clotting at the skin surface wound site, the deeper internal puncture in the vein or artery continues to hemorrhage increasing the likelihood that a hematoma or other vascular complications will occur. Hemostatic patches have not been demonstrated to be effective at a distance in treating punctures resulting from catheterization, but nonetheless hemostatic patches have numerous surgical applications where the patches or fabrics can be applied directly to the wound surfaces on organs exposed during surgical procedures.

Another approach to reducing localized vascular complications associated with catheterization procedures has been the development of devices to aid in the application of hemostatic compositions percutaneously, so that a hemostatic composition is administered in contact with the puncture site. Kipshidze et al. (U.S. Pat. No. 5,437,292) and Van Tassel et al. (U.S. Pat. No. 6,193,670 B1) each invented a device for sealing catheter puncture sites in blood vessels. Such a device typically administers a plug composed of collagen or fibrin that extends from the site of the puncture in the vein or artery through the catheter sheath tract to the skin surface. Numerous variations of such device have been developed where the puncture site is sealed with a suture (Wood et al. U.S. Pat. No. 5,746,755), or where the puncture in the blood vessel is sealed from within the blood vessel lumen (Redmond et al. U.S. Ser. No. 2002/0006429 A1). Gwechenberger, Silber, Camenzind, and Sanborn each provided a comparison of sealant devices employed with compression compared with manual compression alone (Camenzind et al, 1994, Journal of the American College of Cardiology. 24(3):655-662; Gwechenberger et al., 1997, Angiology. 48(2):121-126; Sanborn et al., 1993, Journal of the American College of Cardiology. 22(5):1273-1279; Silber et al., 1998, Catheterization and Cardiovasular Diagnosis 43:421-427). Nearly, all commercially available devices and patches are suggested for use in conjunction with compression. The main disadvantage of such devices is the invasive manner in which the compositions or sutures are applied.

Although several hemostatic devices are commercially available, complication rates with theses closure devices are similar to conventional manual compression (Olade et al., 2002, Emedicine Journal, 3(3):1-13). Devices and methods which do not suture the catheter arterial puncture, but plug the catheter tract with collagen from the skin surface to the arterial puncture site have also been shown to be no more effective than manual compression alone (Camenzind et al., 1994, Journal of the American College of Cardiology. 24(3):655-662). Whether arterial puncture closure devices or hemostatic patches are used to treat a breach or puncture in a vein or artery, there remains a need for reducing the incidence of life threatening complications associated with catheterization and other procedures which has been a persistent medical problem which bespeaks the need for new treatments.

3. SUMMARY OF THE INVENTION

The present invention provides methods and compositions for treatment for a breach or puncture in a vein or artery that would decrease the occurrence of hematomas and other localized vascular complications. Without being bound by any theory, the inventors believe that the compositions and methods of the invention are effective in tissues beyond the site of contact with the skin surface wound relative to the devices and patches of the art. Thus, the compositions and methods of the invention provide the advantage and decreased likelihood of localized vascular complications. The main feature of the methods and compositions of the invention over the existing hemostatic patches and devices is the non-invasive manner in which the compositions function and can be applied.

Accordingly, the present invention provides a method for treating a breach or puncture in a vein or artery of a patient that comprises: a) applying topically to the patient's skin over a wound contiguous with the breach or puncture in the vein or artery a composition comprising an effective amount of a vasoconstrictor, wherein the vasoconstrictor does not comprise a poly-$\beta$-1$\rightarrow$4 N-acetylglucosamine polymer or derivative thereof, and concurrently b) applying compression to the breached or punctured vein or artery, wherein a cessation or reduction of blood flow out of the breach or puncture in the vein or artery is achieved at a greater rate or in a reduced period of time than applying compression in conjunction with a topical barrier-forming material without a vasoconstrictor. In related embodiments, the composition further comprises a coagulant.

In other embodiments of the present invention, a method for achieving a cessation of blood flow or sealing of a breach or puncture in a vein or artery and a cessation of blood flow or sealing of a skin surface wound that is contiguous with the breach or puncture comprises: a) applying topically to the patient's skin over a wound contiguous with a breach or puncture in a vein or artery a composition comprising a vasoconstrictor or coagulant, wherein the vasoconstrictor or coagulant does not comprise a poly-$\beta$-1$\rightarrow$4 N-acetylglucosamine polymer or derivative thereof; b) concurrently applying compression to the breached or punctured vein or artery; and c) recording the amount of blood flow from the wound and the puncture, wherein an amount of the vasoconstrictor or coagulant is effective to increase sealing or increase cessation of blood flow from the breach or puncture in the vein or artery and increase sealing or increase cessation of blood flow from the skin surface wound, in comparison to applying compression in conjunction with a topical barrier-forming material without a vasoconstrictor.

In other embodiments of the present invention, a method for treating a breach or puncture in a vein or artery of a patient, comprises: a) applying topically to the patient's skin over a wound contiguous with the breach or puncture in the vein or artery a composition comprising an effective amount of a coagulant, wherein the coagulant does not comprise a poly-$\beta$-1$\rightarrow$4 N-acetylglucosamine polymer or derivative thereof; and concurrently b) applying compression to the breached or punctured vein or artery, wherein a cessation or reduction of blood flow out of the breach or puncture in the vein or artery is achieved at a greater rate or in a reduced period of time than applying compression in conjunction with a topical barrier-forming material without a coagulant.

In related embodiments, the compositions of the invention further comprise an anti-fungal agent, an antibacterial agent, and/or collagen. In yet other related embodiments, the composition further comprises a pharmaceutical carrier. In certain embodiments, the composition is formulated as a gel, solid, liquid, sponge, foam, spray, emulsion, suspension, or solution. In yet other related embodiments, the composition further comprises a neutral liquid, neutral gel or neutral solid. In preferred embodiments, the composition further comprises a neutral solid and the neutral solid is a gauze. In other preferred embodiments, the composition is in the form of a coating on a neutral solid. In yet other preferred embodiments the barrier-forming material is a gauze.

The present invention provides for use of a coagulant with the compositions, methods, and kits of the present invention described herein, wherein the coagulant is selected from the group consisting of alpha-2-antiplasmin, alpha-1-antitrypsin, alpha-2-macroglobulin, aminohexanoic acid, aprotinin, a source of Calcium ions, calcium alginate, calcium-sodium alginate, casein kinase II, chitin, chitosan, collagen, cyanoacrylates, epsilon-aminocaproic acid, factor XIII, fibrin, fibrin glue, fibrinogen, fibronectin, gelatin, living platelets, methacrylates, plasminogen activator inhibitor-1 (PAI-1), plasminogen activator inhibitor-2 (PAI-2), plasmin activator inhibitor, plasminogen, platelet agonists, protamine sulfate, prothrombin, an RGD peptide, sphingosine, a sphingosine derivative, thrombin, thromboplastin, and tranexamic acid. In another embodiment of the invention, any coagulant that can be used in any of the methods of the present invention described herein.

The present invention provides for use of a vasoconstrictor with the compositions, methods, and kits of the present invention described herein, wherein the vasoconstrictor is selected from the group consisting of endothelin, endothelin-1, epinephrine, adrenaline, metaraminol bitartrate (Aramine™), dopamine HCl (Intropine™), isoproterenol HCl (Isuprel™), norepinephrine (Levophed™), phenylephrine, Serotonin™, thromboxane, norepinephrine, prostaglandin, methergine, oxytocin, isopreland U-46619, papaverine, yohimbine, visnadin, khellin, bebellin, and nicotinate derivatives. In an alternative embodiment, the present invention provides for a vasoconstrictor that can be used with the methods of the present invention described herein, with the proviso that the vasoconstrictor is not epinephrine.

In certain embodiments of the methods of the invention, the patient is a human.

In certain embodiments of the compositions, methods, and kits of the invention, a film or membrane is used in conjunction with the vasoconstrictor and/or coagulant. In certain modes of theses embodiments, the film or membrane comprises a barrier-forming material. In yet other embodiments, the composition is formulated as a mat, string, microbead, microsphere, and/or microfibril.

The methods and compositions of the present invention provide for a composition that comprises a vasoconstrictor and or coagulant and further comprises a biodegradable material. In certain embodiments, the biodegradable material is selected from the group consisting of polyanionic polysaccharides, alginic acid, collagen, polyglycolide, polylactide, polycaprolactone, dextran and copolymers thereof, polyglycolide, polylactide, polydioxanones, polyestercarbonates, polyhydroxyalkonates, polycaprolactone, and copolymers thereof. In certain embodiments, the compositions of the invention are coated with one or more of these biodegradable materials. In other embodiments, the compositions of the invention are co formulated with one or more of these biodegradable materials.

In preferred embodiments, the methods of the invention comprise the step of administering to the patient an anticoagulant, and then applying topically to the patient's skin over a wound contiguous with the breach or puncture in the vein or artery a composition comprising an effective amount of a vasoconstrictor, wherein the vasoconstrictor does not comprise a poly-$\beta$-1→4 N-acetylglucosamine polymer or derivative thereof, and concurrently carrying out the step of applying compression to the breached or punctured vein or artery. In related preferred embodiments, the anticoagulant administered to a patient is selected from the group consisting of coumadin, heparin, nadroparin, aspirin, and a thrombolytic agent. In other related embodiments, the composition further comprises protamine sulfate in an amount effective to neutralize heparin. In other preferred embodiments, the patient is administered the anticoagulant comprising aspirin together with another agent selected from the group consisting of coumadin, heparin, nadroparin, and a thrombolytic agent. In yet other preferred embodiments, the anticoagulant comprises one or more of coumadin, heparin, nadroparin, aspirin, or a thrombolytic agent.

The methods described herein can be used to treat a breach or puncture in any vein or artery, including but not limited to the femoral, radial, brachial, or axillary artery, and the femoral, internal jugular, or subclavian vein. Descriptions and depictions of the locations of such blood vessels can be found in anatomy references including but not limited to Leonard, C. H. 1983, The concise Gray's Anatomy, Chartwell books, Secaucus, N.J.

In certain preferred embodiments of the methods of the invention, the compression that is applied is manual compression. In other embodiments of the present invention, the compression is mechanical compression. In related embodiments, the compression is applied to the vein or artery proximal of the puncture or breach. In other related embodiments, the compression is applied at the site of application of the composition. In yet other embodiments, the compression is applied with a compression bandage. In preferred embodiments of the present invention, the methods of the invention further comprise, repeating the step of application of compression to the breached or punctured vein or artery.

In certain embodiments of the present invention, the rate of cessation or reduction of blood flow out of the breach or puncture in the vein or artery achieved by the present methods involving the topical use of a vasoconstrictor is at least 10% greater than without the vasoconstrictor. In other embodiments of the present invention, the rate of cessation or reduction of blood flow out of the breach or puncture in the vein or artery is 20%, 30%, 40%, or 50% greater than applying compression in conjunction with a topical barrier-forming material without a vasoconstrictor. In preferred embodiments of the present invention, the vein or artery is breached or punctured by a catheter.

In certain embodiments of the present invention, the time to achieve cessation or reduction of blood flow out of the breach or puncture in the vein or artery is 10% less than applying compression in conjunction with a topical barrier-forming material without a vasoconstrictor. In other embodiments of the present invention, the time to achieve cessation or reduction of blood flow out of the breach or puncture in the vein or artery is 20%, 30%, 40%, or 50% less than applying compression in conjunction with a topical barrier-forming material without a vasoconstrictor. In preferred embodiments of the present invention, the vein or artery is breached or punctured by a catheter.

The methods of the invention can be used to treat vascular breaches or punctures in a patient by applying a composition of the invention to a portion of the patient's skin that is contiguous with the breach or puncture. The portion of the skin can be at any distance from the breach or puncture, as long as the composition of the invention is capable of exerting an effect on the wound healing process. In certain embodiments, the distance is approximately 10, 9, 8, 7, 6, 5, 4, 3, 2 or 1 cm from the puncture in a vein or artery. In a preferred embodiment, the breach or puncture in a vein or artery is approximately 8, 9, or 10 cm from a contiguous skin wound site. In another preferred embodiment, the breach or puncture in a vein or artery is approximately 4, 3, 2, or 1 cm from a contiguous skin wound site. In yet another preferred embodiment, the breach or puncture in a vein or artery is approximately 7, 6, or 5 cm from a contiguous skin wound site.

The present invention provides methods for decreasing the occurrence of localized vascular complications in a patient. One such method comprises the following steps, a) applying topically to the patient's skin over a wound contiguous with a breach or puncture in a vein or artery a composition comprising a vasoconstrictor or coagulant, wherein the vasoconstrictor or coagulant does not comprise a poly-$\beta$-1→4 N-acetylglucosamine polymer or derivative thereof; b) concurrently applying compression to the breached or punctured vein or artery; and c) recording the occurrence of localized vascular complications, wherein an amount of the vasoconstrictor or coagulant is effective to cause sealing of the breach or puncture in the vein or artery, reducing the rate of localized vascular complications in comparison to applying compression in conjunction with a topical barrier-forming material without a vasoconstrictor. In certain preferred embodiments, the rate of cessation or reduction of blood flow out of the breach or puncture in the vein or artery is at least 50% greater than applying compression in conjunction with a topical barrier without a vasoconstrictor. In other preferred embodiments, the rate of cessation or reduction of blood flow out of the breach or puncture in the vein or artery is at least 10%, 20%, 30%, 40%, 50%, 60%, or 70% greater than applying compression in conjunction with a topical barrier without a vasoconstrictor. In certain preferred embodiments, the time to achieve cessation or reduction of blood flow out of the breach or puncture in the vein or artery is at least 50% less than applying compression in conjunction with a topical barrier without a vasoconstrictor. In other preferred embodiments, the time to achieve cessation or reduction of blood flow out of the breach or puncture in the vein or artery is at least 10%, 20%, 30%, 40%, 50%, 60%, or 70% less than applying compression in conjunction with a topical barrier without a vasoconstrictor.

The present invention further provides a pharmaceutical composition for topically treating a breach or puncture in a vein or artery wherein the pharmaceutical composition comprises: a) an effective amount of a vasoconstrictor, wherein the vasoconstrictor does not comprise a poly-β-1→4 N-acetylglucosamine polymer or derivative thereof; and b) a pharmaceutically acceptable carrier. In certain preferred embodiments, the pharmaceutical composition further comprises a coagulant. In other preferred embodiments, the pharmaceutical composition further comprises a neutral liquid, neutral gel and/or neutral solid. As used herein in relation to all embodiments of the invention, a neutral liquid, neutral gel and/or neutral solid means such agents have no activity or are inactive with respect to processes involved in hemostasis. The pharmaceutical composition can further comprise a gauze.

The present invention further provides a kit useful for practicing the present methods that comprises in one or more containers a composition useful for treating a breach or puncture in a vein or artery, that comprises: a) an effective amount of a vasoconstrictor, wherein the vasoconstrictor does not comprise a poly-β-1→4 N-acetylglucosamine polymer or derivative thereof; and b) a pharmaceutically acceptable carrier, and instructions for topically treating a breach or puncture in a vein or artery. The composition can further comprise a coagulant, a neutral liquid, a neutral gel and/or a neutral solid. In a preferred embodiment the composition further comprises a gauze. In another preferred embodiment the composition further comprises gelatin.

The present invention yet further provides a pharmaceutical composition for topically treating a breach or puncture in a vein or artery wherein the pharmaceutical composition comprises: a) an effective amount of a vasoconstrictor, wherein the vasoconstrictor does not comprise a poly-β-1→4 N-acetylglucosamine polymer or derivative thereof, and b) wherein the vasoconstrictor is formulated into a barrier, membrane, or film. The pharmaceutical composition can further comprise a coagulant. The pharmaceutical composition can further comprise a neutral liquid, neutral gel and/or neutral solid. In a preferred embodiment the composition further comprises gelatin.

The present invention yet further provides a kit useful for practicing the present methods that comprises in one or more containers a composition that comprises: a) an effective amount of a vasoconstrictor, wherein the vasoconstrictor does not comprise a poly-β-1→4 N-acetylglucosamine polymer or derivative thereof; and b) wherein the vasoconstrictor is formulated into a barrier, membrane, or film, and instructions for topically treating a breach or puncture in a vein or artery. The composition can further comprise a coagulant, a neutral liquid, a neutral gel and/or a neutral solid. In a preferred embodiment the composition further comprises gauze. In another preferred embodiment the composition further comprises gelatin.

In preferred embodiments, the compositions and methods of the invention described herein can be used in treatment of catheter-induced punctures in veins or arteries. The treatment can comprise reducing hemostasis time, reducing the flow of blood from the catheter puncture in the blood vessel, and reducing the occurrence of localized vascular complications.

In particular, the methods of the present invention described herein are useful for the treatment of cardiac catheterization wounds. Such wounds commonly result from diagnostic or therapeutic cardiac intervention procedures such as coronary angiography and angioplasty. In one embodiment, a method for treating a puncture in a vein or artery resulting from a cardiac catheterization procedure in a patient comprises: a) applying topically to the patient's skin over a catheter exit site a composition comprising an effective amount of a vasoconstrictor and/or coagulant, wherein the vasoconstrictor and/or coagulant does not comprise a poly-β-1→4 N-acetylglucosamine polymer or derivative thereof, and wherein the catheter exit site is contiguous with the catheter puncture in the vein or artery by approximately 1-10 cm; and concurrently b) applying compression to the punctured vein or artery, wherein a cessation or reduction of blood flow out of the breach or puncture in the vein or artery is achieved at a rate 30%-50% greater than applying compression in conjunction with a topical barrier-forming material without a vasoconstrictor and/or coagulant.

In another embodiment, a method for treating a puncture in a vein or artery resulting from a cardiac catheterization procedure in a patient comprises: a) applying topically to the patient's skin over a catheter exit site a composition comprising an effective amount of a vasoconstrictor and/or coagulant, wherein the vasoconstrictor and/or coagulant does not comprise a poly-β-1→4 N-acetylglucosamine polymer or derivative thereof, and wherein the catheter exit site is contiguous with the catheter puncture in the vein or artery by approximately 1-10 cm; and concurrently b) applying compression to the punctured vein or artery, wherein a cessation or reduction of blood flow out of the breach or puncture in the vein or artery is achieved in a measure of time that is 30%-50% less than applying compression in conjunction with a topical barrier-forming material without a vasoconstrictor and/or coagulant.

The methods of the present invention are also useful for reducing the number and size of hematomas such as those resulting from a cardiac catheterization procedure in a patient. The methods of the present invention are also useful for inhibiting the formation of hematomas such as those resulting from a cardiac catheterization procedure in a patient. As used herein in the context of the invention, "inhibiting the formation of hematomas" means decreasing the probability that a hematoma will form or decreasing the probability that hematomas of a large size, e.g., greater than 3 cm, will form. In one embodiment, a method of reducing the occurrence of a hematoma following cardiac catheterization comprises: a) applying topically to the patient's skin over a catheter exit site contiguous by 1-10 cm with a catheter puncture in a vein or artery a composition comprising an effective amount of a vasoconstrictor and/or coagulant, wherein the vasoconstrictor and/or coagulant does not comprise a poly-β-1→4 N-acetylglucosamine polymer or derivative thereof; b) concurrently applying compression to the punctured vein or artery thereby reducing the occurrence of hematomas after cardiac catheterization. In certain embodiments, a reduction in the occurrence of hematomas is measured by recording the number of hematomas formed in a sample patient population, in comparison to a sample patient population wherein compression is applied to the patients in conjunction with a topical barrier-forming material without a vasoconstrictor and/or coagulant.

3.1 DEFINITIONS

"Localized vascular complications"—Localized vascular complications include hematomas, pseudoaneurysms, and AV fistula formations, and other medical conditions associated with a breach or puncture in a vein or artery.

"Hematoma"—Hematomas are produced by of the invasion of other tissues by blood tissue normally localized inside the blood vessels, resulting in swelling of the invaded tissues and tissues surrounding the invaded tissues.

"Barrier-forming material"—A barrier-forming material is any material that can be placed on the surface of the skin over a wound and physically impede or reduce blood flow from the wound.

"Concurrently"—concurrently as used herein, in relation to applying a composition of the invention and compression to a patient, means either applying compression and a composition of the invention topically to a wound site on a patient at the same time, or applying a composition topically to a wound site on a patient immediately (i.e. any period of time less than 1 minute, or less than 2 minutes) followed by application of compression to the wound site on a patient. For example, if the composition of the invention is formulated as a barrier forming material, then the composition and the compression can be applied at the same time. If the composition is for example a gel, the gel can be applied to the wound site followed immediately by compression, or the gel might be applied to a barrier-forming material such as gauze and the treated gauze can then be applied at the same time as compression. In all examples the application of the composition and compression is defined as concurrent.

4. BRIEF DESCRIPTION OF THE FIGURES

FIG. 1. Ultrasonography of a human femoral artery. Top of image correlates with skin surface of patient, and cross hair symbol marks the center of the blood vessel at 2.67 cm below the skin surface.

5. DETAILED DESCRIPTION OF THE INVENTION

The present invention is based upon the concept of treating a breach or puncture in a vein or artery from a distance via a skin surface wound contiguous with the breach or puncture. The present methods encompass topically applying to the skin surface wound a composition with vasoconstrictive and/or coagulating properties in conjunction with application of compression to the site or an proximal site of the vein or artery to reduce blood flow. The methods described herein seal or heal of the breach or puncture at a greater rate or in less time in comparison to available non-invasive treatments, i.e. hemostatic patches, compression. The invention also encompasses one or more compositions that can be used in the methods of the invention and kits that comprise one or more of the compositions of the invention for use in treating a breach or puncture in a vein or artery.

Thus, the present invention provides a solution for the problem of localized vascular complications, such as hematomas, pseudoaneurysms, and AV fistula formations, associated with treating a breach or puncture in a vein or artery. In particular, the methods of the invention described herein, are an improvement over both hemostatic patches and arterial closure devices in treating wounds resulting from medical procedures, including but not limited to cardiac catheterization procedures. Whereas the available hemostatic patches act directly at the site of contact with the wound, and only indirectly act on the catheter puncture in the artery or vein by decreasing blood flow, without being bound by any theory, the inventors believe that, the compositions and methods of the invention act on the catheter puncture in the artery or vein from a distance and stop or reduce blood flow from the internal puncture site at a greater rate or in less time than presently known devices, decreasing the likelihood of hematoma formation. For example a soluble vasoconstrictor may act on receptors present in a blood vessel, resulting in a constriction of the blood vessel. The methods of the present invention are an improvement over the invasive arterial closure devices used following cardiac catheterization. The advantages offered include the ease of carrying out the method steps, since no suture machines or application devices need be applied subcutaneously, and a decreased likelihood of hematoma formation. The non-invasive methods of the invention also minimize the risk of infections that can occur when foreign objects, such as the available arterial closure devices are inserted through the layers of a patients skin.

5.1 Injuries for Treatment by the Present Methods and Compositions

The present invention provides methods for treatment of a breach or puncture in a vein or artery. The breach or puncture may be a wound of any origin or cause. In an embodiment of the invention, the breach or puncture in a vein or artery is caused by an object such as a bullet, knife, or surgical instrument. In a preferred embodiment the object that causes a breach or puncture in the vein or artery is a catheter. In yet another preferred embodiment the puncture is the result of a cardiac catheterization procedure. Arteries whose breaches or punctures may be treated by the present methods and compositions include, but are not limited to, the femoral, radial, brachial, and axillary arteries. Veins whose breaches or punctures may be treated by the present methods and compositions include, but are not limited to, the femoral, internal jugular, and subclavian veins.

Generally, when the breach or puncture in the vein or artery being treated by the present methods and compositions results from cardiac catheterization, the vein or artery will have a breach or puncture can be caused by a smaller diameter catheter. Examples of smaller diameter catheters include catheters ranging from 4 F to 6 F in size (F=French Units, where 1 F is equal to 0.33 mm). In another embodiment of the invention, the breach or puncture may be caused by a larger-diameter catheter ranging in size from 7 F to 11.5 F (Sanborn et al., 1993, Journal of the American College of Cardiology. 22(5):1273-1279). Preferably, the artery is larger than a catheter between 6 F and 8 F in size. In such embodiments where a breach or puncture is the result of catheterization, the methods and compositions of the invention can be used to treat punctures or breaches cause by various types of catheters, including but not limited to a Swan-Ganz catheter, a Sones catheter, and a pigtail catheter (Olade et al., 2002, Emedicine Journal, 3(3):1-13).

In certain embodiments, catheters are inserted perpendicular to the skin surface. In other embodiments, a catheter is inserted at an angle that is 20°-40° to the skin surface.

The present methods can be used to treat breaches or punctures in veins or arteries in any mammal including but not limited to a human, dog, horse, cat, rabbit, rat, mouse, pig, cow, monkey or sheep. Preferably the patient is a human.

5.2 Methods for Using the Hemostatic Compositions

The methods of the invention encompass topical administration of a composition comprising a vasoconstrictor or a coagulant to a patient's skin surface at a site of a wound that is contiguous with a breach or puncture in a vein or artery. Compositions of the invention comprising vasoconstrictors and/or coagulants are further described in section 5.5 below, and may include a barrier-forming component that is applied to the skin surface over a wound that is contiguous with a breach or puncture in a vein or artery.

5.2.1 Site of Application of Hemostatic Composition

The present methods for treating vascular wounds can entail a combination of applying pressure and/or a barrier-forming material and a composition of the invention comprising a vasoconstrictor or coagulant agent to a site on the patient's skin surface wound that is contiguous with a breach or puncture in a vascular structure such as a vein or artery. In a preferred embodiment of the invention, a site of application on the skin surface of the composition of the invention, contiguous with a breach or puncture in the vein or artery, is within 10 cm of the site of a breach or puncture in a vein or artery. In another embodiment, the site of application is within approximately 9 cm, 8 cm, 7 cm, 6 cm, 5 cm, 4 cm, 3 cm, 2 cm, or 1 cm of a breach or puncture in the vein or artery. In yet another embodiment, the site of topical application is between 10 cm and 2 cm of a breach or puncture in the vein or artery. In a preferred embodiment the site of topical application is about 1-10 cm from a breach or puncture in the vein or artery.

5.2.2 Applying Compression

Compression can be indirectly applied to a breached or punctured vein or artery in several ways. The present methods for treating vascular wounds can entail a combination of applying pressure and/or a barrier-forming material and a composition of the invention comprising a vasoconstrictor or coagulant agent to a site on the patient's skin surface wound that is contiguous with a breach or puncture in a vascular structure such as a vein or artery. When a vein or artery with a breach or puncture is subject to compression, blood flow and pressure decreases in the vein or artery, allowing the puncture to seal or clot with a decreased likelihood of hematoma formation.

In certain embodiments of the invention, the compression is manual compression. Manual compression can be applied by pressing with the tips of fingers on the skin surface, at a point above an underlying vein or artery, so that the vein or artery is compressed and blood flow is significantly reduced or stopped in the targeted vein or artery. This type of compression can be applied at a site proximal of a breach or puncture in a vein or artery. Typically, an proximal site is between 1 and 10 cm proximal of the breach or puncture. The technique of manually pressing on a patients skin at the correct place to reduce blood flow and blood pressure is common in the art and is effective in both humans and other mammals (Camenzind et al, 1994, Journal of the American College of Cardiology. 24(3):655-662; Kipshidze et al., 1998, Journal of Invasive Cardiology. 10(3):133-141; Merino et al., 1992, Catheterization and Cardiovasular Diagnosis 26:319-322; Sanborn et al., 1993, Journal of the American College of Cardiology. 22(5):1273-1279). The manual compression can be optionally applied in combination with application of a composition comprising "a composition of the invention," comprising a vasoconstrictor or coagulant. Such embodiments entail manually compressing to subject a artery or vein to compression concurrently with applying a composition of the invention. Alternatively, manual compression can be applied immediately prior to application of a composition of the invention or immediately after application of a composition of the invention.

In an embodiment of the invention that encompasses a manual compression technique as a part of a method of the invention, the technique may be one wherein pressure is applied with ones fingers or the palm of ones hand directly over a dermotomy site that is contiguous with a breach or puncture in the vein or artery (Sanborn et al., 1993, Journal of the American College of Cardiology. 22(5):1273-1279). In certain embodiments where the wound is caused by a catheter, compression can be applied directly to the wound site at the same angle that the catheter was inserted at. In one embodiment of the invention, manual compression may be applied concurrently with application of the composition. If the composition of the invention is formulated as a barrier-forming material, then the composition and the compression can be applied at the same time. If the composition is for example a gel, the gel can be applied to the wound site followed immediately by compression, or the gel might be applied to a barrier-forming material such as gauze and the treated gauze can then be applied at the same time as compression.

In applying manual compression techniques, the amount of pressure applied and the consistency of pressure force generally varies over time and among individuals applying the pressure. For this reason, it may be preferable to apply compression to a breached or punctured vein or artery mechanically rather than manually, to ensure the consistency of the force of the pressure applied. Several devices have been developed and are commonly used to apply compression, including C-clamps of varying or adjustable force and compression bandages/dressings with attachment of desired weights. Such compression devices may be used in conjunction with the methods and compositions of the invention and can provide a constant application of the desired compression force.

In certain embodiments, compression is either applied first at a site proximal to the wound site to decrease blood flow in the vein or artery with the breach or puncture or compression is first applied to both the proximal site and the wound site simultaneously, in either case the compression applied at the proximal site is later released or decreased while the compression at the wound site is maintained. The time between the application of compression and the release of pressure at the proximal site can be about 15 seconds, 30 seconds, 1 minute, 1.5 minutes, 2 minutes, 2.5 minutes, 3 minutes, 3.5 minutes, 4 minutes, 4.5 minutes, or 5 minutes. In other embodiments, compression is applied and maintained at both the proximal and wound sites.

In another embodiment, where the composition encompasses an adhesive barrier-forming material, the composition can be topically adhered to cover a skin surface wound that is contiguous with a breach or puncture in a vein or artery without applying pressure to compress the vein or artery.

5.2.3 Compression Time

One of the advantages of the methods of the present invention is that the combination of compression and the compositions of the invention results in a reduction in compression time needed to stop or slow the flow of blood from the breach or puncture relative to compression alone. The amount of time for which compression is maintained to achieve hemostasis, i.e. a cessation or lessening of blood flow from a breach or puncture in a vein or artery, is subjected to the size of the wound, the distance from the skin surface, and the amount of pressure applied in compressing the blood vessel. As used herein in connection with the invention, hemostasis means cessation of blood flow from a breach or puncture in a vein or artery. The amount of time for which compression is maintained when carrying out the methods of the invention is shorter in comparison to compression alone or compression without a composition of the invention as measured under comparable circumstances.

In general, when applying a manual compression technique it is preferable to apply adequate but gradually lessening pressure for a period of time between ten and thirty minutes before inspection of the site, with reapplication of pressure as necessary for ten to twenty minute intervals (Camenzind et al, 1994, Journal of the American College of Cardiology. 24(3):655-662; Kipshidze et al., 1998, Journal of Invasive Cardiology. 10(3):133-141; Sanborn et al., 1993, Journal of the American College of Cardiology. 22(5):1273-1279). In certain instances, the period of time for which compression is applied may be greater than 30 minutes. If non-manual compression is employed in the methods of the invention, then a constant pressure may be applied for ten to thirty minutes or more, particularly when applying compression alone. A technique corresponding to stepwise reduction in compression described above can be employed when using for example a C-clamp or compression bandage/dressing, wherein the pressure may be lessened in increments over time as necessary. A fluid-filled balloon connected to a pressure transducer can also be used to measure the amount of pressure applied. The amount of compression force varies for each patient and the type and location of the blood vessel, i.e. vein or artery, being treated. Any of the compression techniques described herein can be used in carrying out the methods of the invention, as well as other standard compression techniques.

In contrast, the time for applying compression, manual or otherwise, in conjunction with a composition of the invention is shorter and may be divided into intervals at which to release or partially release pressure for 1-10 seconds in order to record observations to calculate the cessation rate or time of blood from a puncture or breach and/or to calculate the time to seal a puncture or breach. The time intervals may be 5, 10, 15, 20, 25, 30, 35, 40, 45, 50, 55, or 60 seconds in length. Alternatively, the time intervals may be 1, 1.5, 2, 2.5, 3, 3.5, 4, 4.5, 5, 5.5, 6, 6.5, 7, 7.5, 8, 8.5, 9, 9.5, or 10 minutes in length (Silber et al., 1998, Catheterization and Cardiovasular Diagnosis 43:421-427).

In a related embodiment, compression is applied for time intervals of equivalent length in patients receiving the treatment compression alone and those receiving the treatment of compression in conjunction with the composition of the invention.

In an embodiment, the decrease in the amount of time required to achieve cessation or a decrease in blood flow from a breach or puncture in a vein or artery using the methods of the invention in comparison to using compression alone is quantified as a percentage.

Various methods for measuring compression time and compression force can be employed in carrying out the methods of the invention as described in section 5.2.4.

Compression should be applied to the desired vein or artery shortly following the breach or puncture (or immediately following a breach or puncture caused by a medical procedure), or as soon possible in the case of accidental punctures or breaches. For example in one embodiment, caused by a medical procedure, compression is applied immediately after removal of a catheter and a catheter sheath.

In a preferred embodiment of the invention, one or more of the methods encompassed by the invention described herein are effective at achieving a cessation or reduction of blood flow out of a breach or puncture in an artery or vein in 3, 4, 5, 6, 7, 8, 9, or 10 minutes.

The compositions of the invention described herein in section 5.5 are preferably applied concurrently with an initial application of compression. In other embodiments, the compositions can be reapplied at compression time intervals. In other embodiments, compression is applied for a brief time prior to application of a composition of the invention and further compression.

5.2.4 Measurement of Time or Rate of Cessation of Bleeding or Sealing of Breach or Puncture In one embodiment, the rate or time of cessation or reduction of blood flow from a breached or punctured blood vessel achieved using the present methods can be measured by any technique known to those skilled in the art. In certain embodiments, for example when testing the efficacy of the present compositions, the rate or time of cessation or reduction is measured and compared in the absence or presence of a composition of the invention. Preferably, the same technique is utilized when measuring the rate or time of cessation or reduction in the presence or absence of a composition of the invention.

In certain embodiments, the efficacy of the compositions and methods of the invention can be measured by simulating in dogs the cardiac catheterization procedure used in humans. The femoral artery in dogs is particularly desirable for such simulations since it is easily accessible, being located not far beneath the skin surface, and hematomas can be easily visualized in this region. Examples of cardiac catheterization simulations in dogs and determination in such dogs of rate or time of cessation of bleeding are presented in Example 1 of Section 6. Measuring rate or time till cessation of blood flow from a skin wound contiguous with a breach or puncture in a vein or artery is an indirect measurement of the flow of blood from the breach or puncture in the vein or artery. Additional, more direct, techniques that can be used with the methods of the invention described herein to observe cessation of blood flow from the breach or puncture in the vein or artery are taught below in Section 5.3.

The rate of or time to achieve cessation or reduction of blood flow out of the breach or puncture in a vein or artery can be calculated simply as the total number of time intervals required to achieve the effect, provided the time intervals are equivalent for each treatment, i.e. compression alone or compression in conjunction with the composition of the invention. For example if the sum of the number of time intervals required for all patients receiving a first treatment is 8 and if the sum of number of time intervals required for all patients receiving a second treatment is 10, then the percent difference would be 25%. Alternatively, the average time to achieve cessation could be calculated for each treatment group, then compared to determine the percent difference.

In another embodiment, the time to achieve cessation is measured in minutes and/or seconds rather than time intervals. The percent difference between the times measured can be calculated with one of the methods described above for the time intervals method.

Where the time to achieve cessation of blood flow from the breach or puncture in the vein or artery is are measured in minutes and/or seconds, the number of time intervals for which compression is applied may not necessarily be a factor in calculating the time to cessation. Total time from application of treatment to cessation or reduction of blood flow out of breached or punctured veins or arteries can be compared for the two treatment groups. In this embodiment of the invention, compression alone may be initially applied for a longer period of time than compression in conjunction with the composition of the invention, since values for the time to achieve cessation are known in the art for compression alone. The time to achieve cessation or the rate of cessation of blood flow from the breach or puncture in the vein or artery can also be measured for the circumstance where only compression is applied. These measurements can be made by any of the methods described herein, including but not limited to ultrasonography and scintigraphic imaging. For example, compression alone may be applied to a patient for 10 minutes before an observation is recorded, while the patient receiving compression in conjunction with the composition of the invention would require compression to be partially and briefly released to make blood flow observations, in order to obtain data to calculate the time to achieve cessation.

If a set number of compression timer intervals is applied, the percent difference can be calculated based on the number of patients in each treatment group. For example, if compression is applied for two time intervals and 60 of 100 patients receiving a first treatment consisting of compression alone achieve cessation of bleeding from a breach or puncture or sealing of a breach or puncture in a vein or artery after two compression intervals, and 80 of 100 patients receiving a second treatment consisting of compression plus the composition of the invention achieve cessation or sealing of a breach or puncture after two equivalent time intervals, then the percent difference in time to achieve hemostasis would be 20%.

The rate of hematoma occurrence can be calculated with clinical observations. One indicator of hematoma formation is swelling of the skin around the local area of a punctured or breached vein or artery. Alternatively, diagnoses of hematoma or local vascular complications as well as sealing and rates or time to achieve cessation of blood flow from a breach or puncture may also be made with various imaging techniques.

Statistical methodology can be employed to determine if the observed differences are statistically significant. In particular, the differences observed between the rate of cessation or time to achieve cessation or occurrence of vascular complications using the methods of the invention in comparison to compression alone or compression with vasoconstrictors and/or coagulants that do not function at a distance can be analyzed with standard statistical methodology. Statistical significance can be determined with any standard calculated statistic (e.g., a one-tailed t-statistic, a two-tailed t-statistic, a chi-square statistic, an F-statistic, etc.). Standard statistical methodologies suitable for use in connection with the invention include methodologies commonly used in medical analyses and clinical trials. Examples of methodologies can be found in reference publications including but not limited to: Vogt W., 1998, Dictionary of Statistics and Methodology—2nd ed., SAGE Publications; Spiegel, D., J. Myles, and K. R., 2002, Abrams Bayesian Approaches to Clinical Trials and Health Care: Statistics in Practice. Wiley, John & Sons, Incorporated; Cleophas, T. J., A. H. Zwinderman, and T. F. Cleophas, 2002, Statistics Applied to Clinical Trials—2nd ed., Gehan, E. A. A. and N. A. Lemak, 1994, Kluwer Academic Publishers; and Statistics in Medical Research: Developments in Clinical Trials—1st ed., Kluwer Academic Publishers.

In a preferred embodiment of the invention, the time to achieve cessation or reduction of blood flow or the rate of cessation or reduction of blood flow out of a breach or puncture in the vein or artery is achieved at a greater rate or in less time than applying compression in conjunction with a topical barrier-forming material without a vasoconstrictor or coagulant, and without the formation of a hematoma. In another embodiment, the time or rate of cessation or reduction of blood flow out of a breach or puncture in the vein or artery is achieved at a greater rate or in less time than applying compression in conjunction with a topical barrier-forming material without a vasoconstrictor or coagulant, and the rate of hematoma occurrence decreases.

For example, color flow duplex sonography of a puncture site can be used to test for pseudoaneurysms, and AV fistulas (Gwechenberger et al, 1997, Angiology. 48(2):121-126.) Scintigraphic Image Analysis can be employed to examine bleeding and/or hematoma formation at the site of breach or puncture and to determine if a breach or puncture is effectively sealed (Ismail et al., 1995, Catheterization and Cardiovasular Diagnosis 34(1):88-95). Angiogram technology can also be used to examine sealing of a breach or puncture site (Hoekstra et al., 1998, Biomaterials. 19:1467-1471). With imaging analyses as described herein and in the examples section, the time or rate and percent difference in rates or times of cessation or reduction of blood flow out of a breach or puncture in the vein or artery can be calculated without releasing compression to make observations.

In embodiments where the femoral artery is punctured, distal pulse measurements can be used to determine if effective closure of the puncture has been achieved. Similar techniques can be used on other arteries or veins.

In one aspect of the invention, the rate of cessation or reduction of blood flow out of a breach or puncture in the vein or artery when employing the methods and compositions of the invention is 10% greater than applying compression in conjunction with a topical barrier or gauze without a vasoconstrictor or coagulant. In a related aspect of the invention, the rate of cessation or reduction of blood flow out of a breach or puncture in the vein or artery when employing the methods and compositions of the invention is 10% greater than applying compression in conjunction with a topical barrier or gauze comprising less than an effective amount of a vasoconstrictor. In other aspects, the rates as described above are 10%, 15%, 20%, 25%, 30%, 35%, 40%, 45%, 50%, 60%, 70%, 80% or greater.

In one aspect of the invention, the time to achieve cessation or reduction of blood flow out of a breach or puncture in the vein or artery when employing the methods and compositions of the invention is 10% less than applying compression in conjunction with a topical barrier or gauze without a vasoconstrictor or coagulant. In a related aspect of the invention, the time to achieve cessation or reduction of blood flow out of a breach or puncture in the vein or artery when employing the methods and compositions of the invention is 10% less than applying compression in conjunction with a topical barrier or gauze comprising less than an effective amount of a vasoconstrictor. In other aspects, the time as described above is 10%, 15%, 20%, 25%, 30%, 35%, 40%, 45%, 50%, 60%, 70%, 80% or less.

In a preferred embodiment, the methods and compositions of the invention effectively cause a cessation of blood flow from both a breach or puncture site in a vein or artery and from the wound site at the skin surface.

In a another preferred embodiment, the methods and compositions of the invention effectively cause a cessation of blood flow from both a breach or puncture site, cause a cessation of blood flow from the wound site at the skin surface, and decrease the likelihood of localized vascular complications including hematoma formation.

5.2.5 Scintigraphic Image Analysis

Scintigraphic Image Analysis can be employed to examine bleeding and/or hematoma formation at site of breach or puncture and to determine if a breach or puncture is effectively sealed, especially in animal model systems (Ismail et al., 1995, Catheterization and Cardiovasular Diagnosis 34(1): 88-95). For example if the invention is being tested on the femoral arteries of dogs, a camera fitted with a low energy all-purpose collimator can be placed in position over a puncture or breach site. Point sources (~50 uCi 99 mTc) in suitable containers may be used to record the exact position of the leg, for alignment of subsequent images. Dogs are injected through the external jugular venous cannula with autologous technetium-labeled red blood cells, (mean=16.65±3.51 mCi), for which the labeling efficiency is previously tested. The labeled cells are allowed to circulate for 5 minutes before images are taken. Images can be taken at regular time intervals up to 24 hours. Early images can be used to ascertain sealing of a breach or puncture and cessation of blood flow from the breach or puncture, whereas later images can be used to identify hematomas with great efficiency.

5.2.6 Angiography

An angiogram is a test in which a dye, or contrast, is administered to a patient and X-ray imaging is used to look inside blood vessels in order to diagnose or treat lesions involving the blood vessels. Angiogram technology is commonly employed to guide catheters through the femoral artery in cardiac catheterization procedures where the femoral artery is punctured. Angiograms can also be used to examine, in a non-invasive manner, cessation of blood flow from a breach or puncture in a vein or artery, or sealing of such a breach or puncture (Hoekstra et al., 1998, Biomaterials. 19:1467-1471). CT or MRI imaging can also be used to examine sealing of a breach or puncture site and cessation of blood from a breach or puncture in a vein or artery.

5.2.7 Ultrasonography

Various sonography and ultrasonography techniques may be employed with the methods and compositions of the invention to examine bleeding and/or hematoma formation at site of breach or puncture and to determine if a breach or puncture is effectively sealed. FIG. 1 exemplifies another use of ultrasonography, determining the distance between the skin surface and an underlying vein or artery in a human. Duplex ultrasonography has demonstrated useful clinical applications in peripheral arterial testing for lesion localization and quantification of abnormal blood flow. For example, color flow duplex sonography of a puncture site can be used to test for hematoma, pseudoaneurysm, and AV fistula formation (Gwechenberger et al, 1997, Angiology. 48(2):121-126).

5.2.8 Thromboelastography

Thromboelastography is a means of examining the whole process of blood coagulation using whole blood. Thromboelastography is useful in connection with the present invention to determine time to cessation or reduction of blood flow from a breached or punctured vein or artery. In Thromboelastography measurements of time and clot strength are made. The results of the measurements are typically presented in a graph representing the beginning of clot formation to fibrinolysis. The graph represents the time necessary for a clot to form and the tensile strength of a clot. A clot has both viscous and elastic properties, however a thromboelastograph measures only the elastic properties of the clot. Typically clotting time is plotted on the x-axis and clot firmness or elasticity is plotted on the y-axis. The clotting time can be effected by various factors including clotting factor deficiencies, inhibitors, anticoagulants, and low platelets. Graphed measurements typically result in an ovoid shape. The alpha angle is measured between the vertical midline of the ovoid shape to the beginning of clotting time. The alpha angle and the clot formation time indicate how fast the clot structure is forming, which can be effected by clotting factor deficiencies, platelet dysfunction, thrombocytopenia, hypofibrinogenaemia. Maximum clot firmness is defined as the width of the curve at the widest point. Maximum clot firmness can be effected by low platelets or low fibrinogen. Fibrinolysis is measured as a decrease in amplitude from the maximum. Typically a decrease of 15% or more is an indication that fibrinolysis is taking place. Examples of thromboelastographs that can be used in conjunction with the claimed invention include but are not limited to ROTEG™, and TEG (Thromboelastography Coagulation Analyzer, Haemascope corporation, Niles, Ill.). A vasoconstrictor and/or coagulant of the invention can be examined by measuring the time to form a clot and the strength of a clot sealing a breach or puncture in a vein or artery with thromboelastography. The speed and strength of clotting can be used in determining if a breach or puncture in a vein or artery is effectively sealed.

5.2.9 Administration of Anticoagulants

In certain embodiments of the invention, the methods and compositions of the invention may be administered to a patient to whom an anticoagulant in an effective amount to prevent coagulation of blood has been administered. Examples of anticoagulants that may be used in conjunction with the invention include, Coumadin™, Dicumarol™, heparin, nadroparin, aspirin, an antiplatelet drug, or a thrombolytic agent. Typically, full dose of heparinization for more than 12 hours before a medical procedure is common. In other protocols heparin is administered at repeated intervals to ensure that a constant active clotting time is maintained (Falstrom et al., 1997, Catheterization and Cardiovasular Diagnosis 41:79-84). For those patients to whom an anticoagulant has been administered prior to a puncture or breach in a vein or artery, the composition of the invention may further comprise one or more agents that locally neutralize the effect of the administered anticoagulant. In patients to whom heparin has been administered the composition may further comprise protamine sulfate in an amount effective to locally neutralize heparin.

5.3 Pharmaceutical Compositions

The present invention provides pharmaceutical compositions that can be used in the practice of the methods of the invention. The pharmaceutical compositions encompassed by the present invention comprise an effective amount of one or more vasoconstrictors and/or one or more coagulants. The vasoconstrictors and/or coagulants that can be used in the methods of the invention can be any vasoconstrictor and/or coagulant that functions at a distance. The compositions of the invention can be formulated into a wide variety of shapes, sizes and masses. The compositions can additionally include components that have no known vasoconstrictive or coagulant properties.

As used herein, the term "effective amount" means a quantity of a composition comprising a vasoconstrictor and/or coagulant that can be applied topically and function, as a vasoconstrictor and/or a coagulant, at a distance to treat a breach or puncture in an artery or vein. The effectiveness of the amount can be measured by comparing the time to achieve or rate at which blood flow from a breach or puncture in a vein or artery ceases or slows in comparison to compression alone.

In certain embodiments of the invention, the compositions of the invention can comprise combinations of agents in the methods of the invention. In one embodiment, the combination can comprise a vasoconstrictor and a coagulant. In other embodiments, the composition can comprise a greater quantity of vasoconstrictor than coagulant, a greater quantity of coagulant than vasoconstrictor. In yet other embodiments, the compositions comprise an agent that functions as both a vasoconstrictor and coagulant. The term "effective amount," as used herein, also means a total amount of a composition of the invention that is applied in the methods of the invention.

The size, shape, and mass of the composition used to topically treat a breach or puncture in a vein or artery will vary depending on the particular use. A pharmaceutical composition can contain an effective amount of a vasoconstrictor, which unless otherwise indicated, does not comprise a poly-$\beta$-1→4 N-acetylglucosamine polymer or derivative thereof. A pharmaceutical composition of the invention can also contain a pharmaceutically acceptable carrier.

As used herein derivatives of a poly-$\beta$-1→4 N-acetylglucosamine polymer include: a semi-crystalline form of a poly-$\beta$-1→4-acetylglucosamine polymer; a poly-$\beta$-1→4-acetylglucosamine polymer comprising about 50 to about 150,000 N-acetylglucosamine monosaccharides covalently attached in a $\beta$-1→4 conformation, and said polymer has a molecular weight of about 10,000 daltons to about 30 million daltons; a poly-$\beta$-1→4-acetylglucosamine polymer comprising about 50 to about 50,000 N-acetylglucosamine monosaccharides covalently attached in a $\beta$-1→4 conformation, and said polymer has a molecular weight of about 10,000 daltons to about 10 million daltons; a poly-$\beta$-1→4-acetylglucosamine polymer comprises about 50 to about 10,000 N-acetylglucosamine monosaccharides covalently attached in a $\beta$-1→4 conformation, and said polymer has a molecular weight of about 10,000 daltons to about 2 million daltons; a poly-$\beta$-1→4-acetylglucosamine polymer comprising about 50 to about 4,000 N-acetylglucosamine monosaccharides covalently attached in a $\beta$-1→4 conformation, and said polymer has a molecular weight of about 10,000 daltons to about 800,000 daltons; and a semi-crystalline poly-$\beta$-1→4 N-acetylglucosamine polymer comprising at least one N-acetylglucosamine monosaccharide that is deacetylated, and wherein at least 40% of said N-acetylglucosamine monosaccharides are acetylated.

Derivatives of a poly-$\beta$-1→4 N-acetylglucosamine polymer also include compositions that are 100%, 90%, 80%, 70%, 60%, 50%, 40%, 30%, 20%, 10% or less poly-$\beta$-1→4 N-acetylglucosamine. Thus, with varying degrees of purity of a vasoconstrictor and/or coagulant is encompassed by the invention.

In certain embodiments of the invention, the composition of the invention comprises a vasoconstrictor and/or a coagulant with one of more of the following provisos that the composition of the invention does not comprise in certain embodiments:

1. The composition of the invention does not comprise a poly-$\beta$-1→4 N-acetylglucosamine polymer or derivative thereof. The composition does not comprise a poly-$\beta$-1→4 N-acetylglucosamine polymer or derivative thereof and an agent that functions as a vasoconstrictor and/or coagulant
2. The composition of the invention does not comprise a poly-$\alpha$-1→4 N-acetylglucosamine polymer or derivative thereof. The composition does not comprise a poly-$\alpha$-1→4 N-acetylglucosamine polymer or derivative thereof and an agent that functions as a vasoconstrictor and/or coagulant
3. The composition of the invention does not comprise a poly-$\alpha$-1→4 N-acetylglucosamine polymer or derivative thereof and a poly-$\beta$-1→4 N-acetylglucosamine polymer or derivative thereof. The composition does not comprise a poly-$\alpha$-1→4 N-acetylglucosamine polymer or derivative thereof, poly-$\beta$-1→4 N-acetylglucosamine polymer or derivative thereof, and an agent that functions as a vasoconstrictor and/or coagulant
4. The composition of the invention does not comprise chitosan, a chitosan derivative, or compositions natural or synthetic that comprise 10%-100% chitosan or a chitosan derivative. The composition of the invention does not comprise chitosan or a chitosan derivative derived from crustaceans. The composition of the invention does not comprise chitosan or a chitosan derivative derived from crustaceans wherein the chitosan or a chitosan derivative have been purified or modified.
5. The composition does not comprise chitosan or a chitosan derivative that is 80% or more deacetylated. The composition does not comprise chitosan or a chitosan derivative that is 70%-100% deacetylated.
6. The composition does not comprise chitosan or a chitosan derivative that is free of fungal, micro-fungal, and crustacean chitosan or chitosan derivatives.
7. The composition of the invention does not comprise chitin, a chitin derivative, or compositions natural or synthetic that comprise 10%-100% chitin or a chitin derivative. The composition of the invention does not comprise chitin or a chitin derivative derived from crustaceans. The composition of the invention does not comprise chitin or a chitin derivative derived from crustaceans wherein the chitin or a chitin derivative have been purified or modified.
8. The composition does not comprise chitin or a chitin derivative that is 80% or more deacetylated. The composition does not comprise chitin or a chitin derivative that is 70%-100% deacetylated.
9. The composition does not comprise chitin or a chitin derivative that is free of fungal, micro-fungal, and crustacean chitin or chitin derivatives.
10. The composition does not comprise one or more coagulants, for example: alpha-2-antiplasmin, alpha-1-antitrypsin, alpha-2-macroglobulin, aminohexanoic acid, aprotinin, a source of Calcium ions, calcium alginate, calcium-sodium alginate, casein kinase II, chitin, chitosan, collagen, cyanoacrylates, epsilon-aminocaproic acid, Factor XIII, fibrin, fibrin glue, fibrinogen, fibronectin, gelatin, living platelets, methacrylates, PAI-1, PAI-2, plasmin activator inhibitor, plasminogen, platelet agonists, protamine sulfate, prothrombin, an RGD peptide, sphingosine, a sphingosine derivative, thrombin, thromboplastin, and/or tranexamic acid.
11. The composition does not comprise epinephrine.

In certain embodiments of the invention, the composition of the invention comprises a vasoconstrictor and/or a coagulant with one of more of the above provisos in certain embodiments.

In one embodiment, compositions of the invention encompass purified vasoconstrictors and/or coagulants, which may be about 100%, 90%, 80%, 70%, 60%, 50%, 40%, 30%, or 20% pure. In a related embodiment, compositions of the invention encompass purified vasoconstrictors and/or coagulants, which range between 100% and 20% in purity. In a preferred embodiment, the vasoconstrictors and/or coagulants is 90-100% purified. In another embodiment, the composition can consist of approximately 100%, 90%, 80%, 70%, 60%, 50%, 40%, 30%, 20%, 10% or less of a vasoconstrictor or coagulant. In a related embodiment, the composition can consist of between 100%, and 10% or less of a vasoconstrictor or coagulant. Thus, the use of a vasoconstrictor and/or coagulant with varying degrees of purity is encompassed by the invention.

Vasoconstrictors and/or coagulants that function at the desired distance can be identified using the methods described herein. For example, the cardiac catheterization procedure simulation in dogs described in Example 1, of Section 6 can be used to measure the effect of potential vasoconstrictors and/or coagulants at varying distances. The only portion of the procedure that needs to actually be simulated is the puncture of a vein or artery with a catheter, mechanical observation or manipulation to observe the vasculature associated with the heart is not necessary. The identification of vasoconstrictors and/or coagulants that function at varying distances can be achieved by selecting veins or arteries at specific distances beneath the skin surface for catheter puncture. The distance of such veins or arteries can be determined by imaging techniques such as those disclosed in Section 5.2.

The composition can be formulated as a gel, solid, liquid, sponge, foam, spray, emulsion, suspension, solution, string, microbead, microsphere, or microfibril. The pharmaceutical compositions of the invention can include a pharmaceutically acceptable carrier, a neutral liquid, neutral gel or neutral solid. In certain preferred embodiments, wherein the composition has been formulated as a barrier, membrane, or film or the composition has been added to a barrier, membrane, or film, the neutral solid or solid composition can be provided as a barrier, membrane, or film. A barrier, membrane, or film can be supplied in a variety of standard sizes, which can be further cut and sized to the area being treated. The barrier, membrane, or film can be a conventional bandage or gauze to which the composition of the invention is added or coated on, prior to application to the patient. Alternatively, the composition can be formulated as a barrier, membrane, or film made out of strings, microbeads, microspheres, or microfibrils, or the composition can be formulated as a barrier-forming mat.

The pharmaceutical compositions of the invention can include a backing. For example, if the composition is formulated as a patch, a backing can be adhered to the patch. The backing can be coated or embedded with any adhesive compound so that areas of the backing that contact the skin will adhere the backing and the attached composition of the invention to the skin surface of the patient. The type of adhesive used can be any type of medically acceptable adhesive. Such backings can be made of natural polymers or synthetic materials. Natural polymers from which the backing can be made include but are not limited to cellulose and xylan. Synthetic materials from which the backing can be made include but are not limited to polyurethane, Teflon, Dacron, stainless steel mesh screen, and a polyester woven fabric. Preferably the backing and adhesive are porous to areas which contact the skin to allow diffusion of oxygen. The backing can also serve as a surface upon which manual compression can be applied.

The composition may be formulated as a barrier-forming material that forms a barrier to blood. The composition can coat, be added to, or integrated into a barrier-forming material that forms a barrier to blood. In one embodiment, the pharmaceutical composition comprises a patch made of barrier-forming materials that are embedded with one or more coagulant and/or vasoconstrictor agent(s). In one embodiment, the pharmaceutical composition comprises a gauze embedded with one or more coagulant and/or vasoconstrictor agent(s). In certain embodiments, the pharmaceutical compositions comprise a barrier-forming material embedded or combined with one or more coagulant and/or vasoconstrictor agent(s), wherein the barrier-forming material contains an adhesive so that the material can be adhere to a patient's skin surface. Alternatively, the composition can lack barrier-forming materials.

According to one aspect of the invention, where the composition is formulated as or applied or integrated in a patch, the patch may vary in size. For example, the patch may be about 2 cm$^2$ to about 30 cm$^2$ in area. In certain embodiments, the patch is round, square, or rectangular. In preferred embodiments, the patch is 2 cm×2 cm, 3 cm×3 cm, 4 cm×4 cm, 5 cm×5 cm, or 6 cm×6 cm in size. In other preferred embodiments, the patch can be cut to reduce the size or to create a two dimensional shape as needed. In preferred embodiments, the above described patches can be manufactured for use in the methods, compositions, and kits of the invention for adult patients weighing about 60, 70, 80, or 90 kg.

In related embodiments, the composition of the invention can contain collagen that can act as a sterile carrier.

In a preferred embodiment, the composition may include one or more coagulants. The coagulant(s), for example, can be one or more of the following: alpha-2-antiplasmin, alpha-1-antitrypsin, alpha-2-macroglobulin, aminohexanoic acid, aprotinin, a source of Calcium ions, calcium alginate, calcium-sodium alginate, casein kinase II, chitin, chitosan, collagen, cyanoacrylates, epsilon-aminocaproic acid, Factor XIII, fibrin, fibrin glue, fibrinogen, fibronectin, gelatin, living platelets, methacrylates, PAI-1, PAI-2, plasmin activator inhibitor, plasminogen, platelet agonists, protamine sulfate, prothrombin, an RGD peptide, sphingosine, a sphingosine derivative, thrombin, thromboplastin, and tranexamic acid.

In related embodiments, the composition of the invention can contain an anti-fungal or antibacterial agent, to prevent infection of the wound surrounding the breach or puncture in the vein or artery.

In a preferred embodiment, the composition may include one or more vasoconstrictors. The vasoconstrictor(s), for example, can be one or more of the following: endothelin, endothelin-1, epinephrine, adrenaline, metaraminol bitartrate (for example, manufactured as Aramine™), dopamine HCl (for example, manufactured as Intropine™), isoproterenol HCl (for example, manufactured as Isuprel™), norepinephrine (for example, manufactured as Levophed™), phenylephrine, serotonin, thromboxane, norepinephrine, prostaglandin, methergine, oxytocin, isopreland U-46619, papaverine, yohimbine, visnadin, khellin, bebellin, and nicotinate derivatives.

In certain embodiments, the composition comprises a catalytic surface that accelerates a rate of a chemical reaction between the composition of the invention and endogenous agents involved in hemostasis. The catalytic surface decreases the time to hemostasis and decreases the time to achieve cessation or reduction of blood flow from the breach or puncture in the vein or artery. The catalytic surface binds blood components to form a plug. The catalytic surface comprises a catalyst that is active at a distance, a distance as described herein in the context of the invention. The catalyst can reduce hemostasis time by causing rapid release of vasoconstrictors substances and/or increasing the concentration of vasoconstrictor substances. In other embodiments, the composition comprises a catalytic surface that accelerates a rate of a chemical reaction between endogenous agents involved in hemostasis, such as the conversion of fibrinogen to fibrin. In yet other embodiments, the composition comprises a catalytic surface that accelerates or inhibits endogenous processes involved in hemostasis, such as release of serotonin by platelets or release of prothrombin or chemical signals by damaged tissues. The chemical reaction or cellular process may be involved with vascular constriction that normally follows injury to a blood vessel such as platelet plug formation, i.e. adherence of platelets to the exposed basement membrane and connective tissue, change in shape of platelets from their discoid shape, secretion of ADP, secretion of serotonin, secretion of phospholipid, synthesis of platelet factors, activation of phospholipase C, liberation of Calcium ions, activation of phospholipase A2, liberation of arachidonic acid, secretion of plasma clotting factors. The compositions of the invention can increase nucleation and formation of clots and/ or the phase transition of blood components from liquid to solid during the formation of a clot.

In one embodiment, the catalytic surface comprises fibers that are undissolveable and which are woven into a mat.

In certain embodiments, the compositions of the invention comprise vasoconstrictors and/or coagulants that are evenly distributed throughout the composition, or supplied as a gradient, for example, by combining fibrous pulps containing a range of desired concentrations of vasoconstrictors and/or coagulants to produce a multilayered composition.

The composition of the invention can contain a biodegradable material. Examples of biodegradable materials which can be used in the composition of the invention include polyanionic polysaccharides, alginic acid, collagen, polyglycolide, polylactide, polycaprolactone, dextran and copolymers thereof, polyglycolide, polylactide, polydioxanones, polyestercarbonates, polyhydroxyalkonates, polycaprolactone, and copolymers thereof. Such biodegradable materials may form a barrier-forming portion of the composition, or act as carriers.

The pharmaceutical compositions of the invention can also comprise wound-healing and/or pain-reducing agents. Such agents include anti-inflammatory agents, both steroidal and non-steroidal, such as but not limited to agents which inhibit leukocyte migration into the area of the breach or puncture in the blood vessel (i.e., silver sulfadiazinem acetylsalicylic acid, indomethacin, and Nafazatrom), anti-histamines (i.e., pyrilamine, chlorpheniramine, tetraydrozoline, antazoline, cortisone, hydrocortisone, beta-methasone, dexamethasone, fluocortolone, prednisolone, triamcinolone, indomethacin, and sulindac, its salts and its corresponding sulfide); agents which inhibit free radical formation (i.e., superoxide dismutase (SOD), catalase, glutathione peroxidase, β-carotene, ascorbic acid, transferring, ferritin, ceruloplasmin, and desferrioxamine alpha-tocophenol); and bacteriostatic or bacteriocidal agents (i.e., cefoxitin, n-formamidoyl thienamycin, tetra cyclines, chloramphenicol, neomycin, gramicidin, bacitracin, sulfonamides, gentamycin, kanamycin, amikacin, sisomicin, tobramycin, norfloxican, nitrofurazones, and the combination of flouroalanin/pentizidone).

5.4 Effective Dose

Generally, a therapeutically effective amount of a vasoconstrictor and/or coagulant for use in the methods, compositions, and kits of the invention, will vary with the patients age, condition, and sex, as well as the nature and extent of the condition in the subject, all of which can be determined by one of ordinary skill in the art. For example, the effective dose needed for an infant may differ from an elderly patient, due to the reduced elasticity of blood vessels that accompanies age. The effective dose can also be dependent on the depth beneath the skin surface at which a breach or puncture in a blood vessel is being treated. The dosage of the vasoconstrictor and/or coagulant of the invention can be adjusted to accommodate the particular subject and condition being treated.

In certain embodiments, the effective amount of the vasoconstrictor and/or coagulant does not directly increase or decrease the function of cells involved in wound healing such as but not limited to polymorphonuclear leukocytes, macrophages and fibroblasts.

Toxicity and efficacy of the vasoconstrictor and/or coagulant of the invention can be determined by standard pharmaceutical procedures in cell cultures or experimental animals, e.g., for determining the ED50 (the dose therapeutically effective in 50% of the population). Vasoconstrictors and/or coagulants that exhibit greater therapeutic effect are preferred. In the present instance, vasoconstrictors and/or coagulants that exhibit toxic side effects may be used in carrying out the methods of the invention. The potential damage to unaffected cells is minimized, since the vasoconstrictors and/or coagulants are applied to the site of affected tissue and thereby reduce the risk of side effects.

The data obtained from the cell culture assays and animal studies can be used in formulating a range of dosage for use in humans. The dosage of such vasoconstrictors and/or coagulants lies preferably within a range of concentrations that include the ED50. The dosage may vary within this range depending upon the formulation of the composition, i.e., gel, foam, patch, etc. For any vasoconstrictor used in the method of the invention, the therapeutically effective dose can be estimated initially from tissue or tissue culture assays.

One standard tissue assay is conducted using aortic rings excised from rats. The aorta are then rapidly suspended in a warmed Krebs-Henseleit (KH) buffer consisting of (in mmol/l): 118 NaCl, 4.75 KCl, 2.54 $CaCl_2.2H_2O$, 1.19 $KH_2PO_4$, 1.19 $MgSO_4.7H_2O$, 12.5 $NaHCO_3$, and 10.0 glucose. Isolated vessels can be carefully freed of connective tissue and cut into rings 2-3 mm in length. The rings are then mounted on stainless steel hooks, suspended in a 10-ml tissue bath, and connected to FT-03 force displacement transducers (Grass Instrument, Quincy, Mass.) to record changes in force on a Grass model 7 oscillographic recorder. The baths are filled with KH buffer and aerated at 37° C. with 95% $O_2$+5% $CO_2$. A resting force of 0.5 g is applied to the SMA rings, and then the rings are equilibrated for 90 minutes. During this period, the buffer in the tissue bath is replaced every 15-20 minutes, and the resting force of the vascular rings is adjusted until 0.5 g of pre-load is maintained. After 90 to 120 minutes of equilibration, the rings are exposed to 100 nM U-46619 (9,11-dideoxy-9α-11α-methaneepoxy-prostagalandin $F_{2\alpha}$, Biomol Research Laboratories, Plymouth Meeting, Pa.), a thromboxane $A_2$ mimetic, to generate 1.0 g of developed force. Once a stable contraction is obtained, acetylcholine, a typical endothelium-dependent vasodilator, is added to the bath in cumulative concentrations of 0.1, 1, 10, and 10 nM to assess the integrity of endothelium. After the cumulative response is stabilized, the rings are washed and again allowed to equilibrate to baseline.

This procedure can be used with a vasoconstrictor other than U-46619 to determine the effectiveness of a vasoconstrictor at maintaining vasoconstriction. The procedure can be repeated with varying concentration of a vasoconstrictor to determine effective dosage.

The function of a coagulant can be tested by standard assays. In such assays, normal human blood, without anticoagulant, is drawn and placed in several test tubes. The normal blood, without a composition of the invention, is allowed to clot (usually within 10 minutes). Other samples of normal blood are drawn and one milliliter aliquots are placed in test tubes with descending aliquots of a particular coagulant used in the methods, compositions, and kits of the invention for which one desires to test coagulant properties. With such an assay one can readily determine how many tenths of a milliliter of the coagulant are effective at causing clotting at a greater rate or in less time than blood without a coagulant. Variations on this standard assay can be conducted where the patient has had an anticoagulant introduced into the bloodstream prior to withdrawal of blood. The results can be used to identify coagulant for use in the methods, compositions, and kits of the invention that can accelerate hemostasis, i.e. cessation of flow of blood from a breach or puncture in a vein or artery.

In various embodiments, an amount of vasoconstrictor and/or coagulant used in the methods, compositions, and kits of the invention is an amount that is 0.5-fold, 0.75-fold, 1-fold, 2-fold, 3-fold, 4-fold, 5-fold, 10-fold, 12-fold, 15-fold, 20-fold, 50-fold or 100-fold the effective dosage, for example, the dosage determined to be effective in treating a breach or puncture in a vein or artery when applied at a distance from the breach or puncture.

The vasoconstrictors and/or coagulants can be formulated into solid, liquid or gel-type formulations for topical application. The concentration of vasoconstrictor and/or coagulants in solid, liquid and/or gel-type formulations can be extrapolated from the dosage and the volume or surface area of the formulation to be applied. For example, such compositions can be manufactured for general use for adults, e.g., adults weighing about 50, 60, 70, 80, or 90 kg, and a topical administration area, e.g., of a patch, of about 1-2, 2-4, 4-8, 8-12, 12-15, 15-20, 20-25, or 25-30 $cm^2$, or a topical administration volume, e.g., of a liquid or gel, of about 0.25-0.5, 0.5-1, 1-1.25, 1.25-1.5, 1.5-1.75, 1.75-2, 2-2.5, or 2.5-3 ml. Exemplary concentration calculations are provided in Section 5.4.1, infra.

In embodiments of the invention where the composition of the invention is formulated as, embedded in, or applied to a patch, 100 mg of the vasoconstrictor and/or coagulant may be present in 1 $cm^2$ of the wound-contacting surface of the patch. In other embodiments, the effective amount of a vasoconstrictor and/or coagulant for use in the methods, compositions, and kits of the invention present in 1 $cm^2$ of a patch can be about 0.05 mg, 0.10 mg, 0.25 mg, 0.50 mg, 0.75 mg, 1 mg, 2 mg, 5 mg, 8 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 1000 mg, or 2000 mg. In a preferred embodiment, the effective amount of a vasoconstrictor and/or coagulant of the invention present in 1 $cm^2$ of a patch is between 0.05 mg and 30 mg of the vasoconstrictor and/or coagulant.

In other embodiments, where the vasoconstrictor and/or coagulant of the invention is formulated as, embedded in, or applied to a patch, 100 µg of the vasoconstrictor and/or coagulant may be present in 1 $cm^2$ of the wound-contacting surface of the patch. In other embodiments, the effective amount of a vasoconstrictor and/or coagulant of the invention present in 1 $cm^2$ of a patch can be about 5 µg, 10 µg, 20 µg, 25 µg, 30 µg, 35 µg, 40 µg, 45 µg, 50 µg, 55 µg, 60 µg, 65 µg, 70 µg, 75 µg, 80 µg, 85 µg, 90 µg, 95 g, 100 µg, 105 µg, 110 µg, 115 µg, 120 µg, 125 µg, 130 µg, 135 µg, 140 µg, 145 µg, 150 µg, 155 µg, or 160 µg between about 1 mM and 70 mM. An example of a coagulant that can be effective in such amounts is thrombin. An example of a vasoconstrictor that can be effective in such amounts is endothelin-1.

In preferred embodiments of the present methods and compositions, the dose of a vasoconstrictor and/or coagulant, e.g., on the surface of a patch, regardless of its molecular weight, is about 1 mM to about 70 mM. In certain exemplary embodiments, the dose is about 1 mM to about 10 mM, about 10 mM to about 30 mM, about 30 mM to about 50 mM, or about 50 mM to about 70 mM.

In yet other embodiments, the effective amount of a vasoconstrictor and/or coagulant of the invention is about 1-1000 $IU/cm^2$ wherein the vasoconstrictor and/or coagulant is formulated as, embedded in, or applied to a patch.

In one embodiment, the vasoconstrictor and/or coagulant forms a concentration gradient that decreases from the site of application to the breach or puncture in the vein or artery. For example, in the case of a cardiac catheterization track wound, the vasoconstrictor and/or coagulant can form a concentration gradient through the track wound and promote clot formation throughout the track resulting in an decreased in the time necessary to achieve hemostasis.

In certain embodiments, an effective amount of a vasoconstrictor and/or coagulant of the invention is an amount that activates hemostasis in the presence of a coagulant or an anticoagulant.

In certain embodiments, the effective dose is the dose necessary to initiate clotting with or without compression. In other embodiments, the effective dose is the dose necessary to cause formation of a firm clot that will remain with or without compression. In yet other embodiments, an effective dose can be determined by the strength of the clot, i.e. the time for which the clot holds with or without compression.

Once it has been determined how varying concentrations and amounts of a particular vasoconstrictor and/or coagulant act in vitro, effective vasoconstrictors and/or coagulants can be further tested in animal models for the distance at which they function by methods described in Section 5.5. An effective amount of a vasoconstrictor and/or coagulant that functions at a given distance can be determined by measuring the time to form a clot and the strength of a clot sealing a breach or puncture in a vein or artery with thromboelastography. A series of measurements can be taken varying the concentration or amount of the vasoconstrictor and/or coagulant to determine an effective amount. The distance of a breach or puncture in a vein or artery from the skin surface can also be varied to determine the maximum or optimal effective distance. Such series of measurements can be used to predict how a particular vasoconstrictor and/or coagulant will function at a particular distance, and allow for a determination of effective amount for a desired distance. The distance animal veins or arteries are beneath the skin surface can be determined by imaging techniques such as those disclosed in Section 5.4. The distance at which certain concentrations or amounts of vasoconstrictors and/or coagulants are effective in vivo can be used to extrapolate the effective amount for a desired distance needed for a particular patient, or the limit to the distance at which a particular vasoconstrictor and/or coagulant is effective. Such information can be used to more accurately determine useful doses in humans.

Results from animal models can be extrapolated to determine effective doses for human subjects. Comparing varying concentrations of a vasoconstrictor and/or coagulant in one or more animal models allows for the establishment of dose response curves that can be used to estimate effective amounts in a human, given the particular circumstances of each subject, i.e. distance of wound, size of wound, presence of coagulants or anticoagulants in the blood stream.

Human patients can also be used to determine the distance at which a vasoconstrictor and/or coagulant is effective. For example, ultrasound can be used to visualize the distance a breach or puncture in a vein or artery is from the surface of the skin and determine if blood flow from the breach or puncture has decreased or been eliminated. Ultrasound probes can be used to locate the breached or punctured vein or artery or to image a specific area by aligning the probes with a desired vein or artery. Ultrasound imaging of the breach or puncture site can be combined with Doppler flow analysis. Doppler flow analysis allows for the determination of cessation or reduction of blood flow through the artery or vein. If blood flow through the vein or artery is inhibited, it may cause damage. Thus, combining Doppler flow and ultrasound would allow for a determination of the maximum upper limit of an effective amount of a vasoconstrictor and/or coagulant. For example, if the effect of a coagulant extends into the blood vessel and causes clotting of platelet and cessation of blood within the blood vessel, the effect could be damaging. In another embodiment, the maximum upper limit of an effective amount of a vasoconstrictor and/or coagulant can be measured as the amount of the vasoconstrictor and/or coagulant for use in the methods, compositions, and kits of the invention that causes an increase in cardiac output.

5.4.1 Vasoconstrictor Doses

In certain preferred embodiments, the effective amount of a vasoconstrictor used in the compositions of the methods, compositions, and kits of the invention will vary with the patients age, condition, and sex, as well as the nature and extent of the condition in the subject, all of which can be determined by one of ordinary skill in the art. For example, a patients body weight can be used to determine an effective amount of a vasoconstrictor.

In one embodiment, the composition topically administered to a patient in the methods of the invention comprises an effective amount of the vasoconstrictor Adrenaline™ in a concentration in the range of about 0.000001 mg/kg of patient body weight to about 11 mg/kg of patient body weight. For adults the preferred Adrenaline™ concentration range is about 0.00001 mg/kg to about 0.5 mg/kg. In related embodiments the effective amount of Adrenaline™ is approximately 0.00001 mg/kg, 0.00005 mg/kg, 0.0001 mg/kg, 0.0005 mg/kg, 0.001 mg/kg, 0.005 mg/kg, 0.01 mg/kg, 0.05 mg/kg, 0.1 mg/kg, 0.5 mg/kg, 1.0 mg/kg, 1.5 mg/kg, 2.0 mg/kg, 2.5 mg/kg, 3.0 mg/kg, 3.5 mg/kg, 4.0 mg/kg, 4.5 mg/kg, 5.0 mg/kg, 5.5 mg/kg, 6.0 mg/kg, 6.5 mg/kg, 7.0 mg/kg, 7.5 mg/kg, 8.0 mg/kg, 8.5 mg/kg, 9.0 mg/kg, 9.5 mg/kg, 10.0 mg/kg, 10.5 mg/kg, or 11.0 mg/kg of patient body weight. In related embodiments the effective amount of Adrenaline™ is about 0.00001 mg/kg to 0.0001 mg/kg, 0.001 mg/kg to 0.01 mg/kg, 0.1 mg/kg to 1.0 mg/kg, 2.0 mg/kg to 3.0 mg/kg, 4.0 mg/kg to 5.0 mg/kg, 6.0 mg/kg to 7.0 mg/kg, 8.0 mg/kg to 9.0 mg/kg, or 10.0 mg/kg to 11.0 mg/kg of patient body weight. In related embodiments the effective amount of Adrenaline™ is about 0.00005 mg/kg to 0.0005 mg/kg, 0.005 mg/kg to 0.05 mg/kg, 0.5 mg/kg to 1.5 mg/kg, 2.5 mg/kg to 3.5 mg/kg, 4.5 mg/kg to 5.5 mg/kg, 6.5 mg/kg to 7.5 mg/kg, 8.5 mg/kg to 9.5 mg/kg, or 10.5 mg/kg to 11.5 mg/kg of patient body weight.

In another embodiment, the composition topically administered to a patient in the methods of the invention comprises an effective amount of the vasoconstrictor metaraminol bitartrate in a concentration in the range of about 0.00001 mg/kg of patient body weight to about 1500 mg/kg of patient body weight. For adults the preferred metaraminol bitartrate concentration range is about 0.0005 mg/kg to about 4.5 mg/kg. In related embodiments the effective amount of metaraminol bitartrate is approximately 0.0005 mg/kg, 0.001 mg/kg, 0.005 mg/kg, 0.01 mg/kg, 0.05 mg/kg, 0.1 mg/kg, 0.5 mg/kg, 1.0 mg/kg, 10 mg/kg, 50 mg/kg, 100 mg/kg, 150 mg/kg, 200 mg/kg, 300 mg/kg, 400 mg/kg, 500 mg/kg, 600 mg/kg, 700 mg/kg, 800 mg/kg, 900 mg/kg, 1000 mg/kg, 1100 mg/kg, 1200 mg/kg, 1300 mg/kg, 1400 mg/kg, or 1500 mg/kg of patient body weight. In related embodiments the effective amount of metaraminol bitartrate is about 0.0005 mg/kg to 0.005 mg/kg, 0.05 mg/kg to 0.5 mg/kg, 50 mg/kg to 150 mg/kg, 300 mg/kg to 500 mg/kg, 700 mg/kg to 900 mg/kg, 1100 mg/kg to 1300 mg/kg, or 1300 mg/kg to 1500 mg/kg of patient body weight. In related embodiments the effective amount of metaraminol bitartrate is about 0.001 mg/kg to 0.01 mg/kg, 0.1 mg/kg to 1.0 mg/kg, 10 mg/kg to 100 mg/kg, 200 mg/kg to 400 mg/kg, 600 mg/kg to 800 mg/kg, 1000 mg/kg to 1200 mg/kg, or 1200 mg/kg to 1400 mg/kg of patient body weight.

In one embodiment, the composition topically administered to a patient in the methods of the invention comprises an effective amount of the vasoconstrictor dopamine HCl in a concentration in the range of about 0.00001 mg/kg of patient body weight to about 150 mg/kg of patient body weight. For adults the preferred dopamine HCl concentration range is about 0.0005 mg/kg to about 10 mg/kg. In related embodiments the effective amount of dopamine HCl is approximately 0.0005 mg/kg, 0.001 mg/kg, 0.005 mg/kg, 0.01 mg/kg, 0.05 mg/kg, 0.1 mg/kg, 0.5 mg/kg, 1.0 mg/kg, 10 mg/kg, 20 mg/kg, 30 mg/kg, 40 mg/kg, 50 mg/kg, 60 mg/kg, 70 mg/kg, 80 mg/kg, 90 mg/kg, 100 mg/kg, 110 mg/kg, 120 mg/kg, 130 mg/kg, 140 mg/kg, or 150 mg/kg of patient body weight. In related embodiments the effective amount of dopamine HCl is about 0.0005 mg/kg to 0.005 mg/kg, 0.05 mg/kg to 0.5 mg/kg, 10 mg/kg to 30 mg/kg, 50 mg/kg to 70 mg/kg, 90 mg/kg to 110 mg/kg, or 130 mg/kg to 150 mg/kg of patient body weight. In related embodiments the effective amount of dopamine HCl is about 0.001 mg/kg to 0.01 mg/kg, 0.1 mg/kg to 1.0 mg/kg, 10 mg/kg to 20 mg/kg, 40 mg/kg to 60 mg/kg, 80 mg/kg to 100 mg/kg, or 120 mg/kg to 140 mg/kg of patient body weight.

In one embodiment, the composition topically administered to a patient in the methods of the invention comprises an effective amount of the vasoconstrictor isoproterenol HCl in a concentration in the range of about 0.00001 mg/kg of patient body weight to about 150 mg/kg of patient body weight. For adults the preferred isoproterenol HCl concentration range is about 0.0005 mg/kg to about 5 mg/kg. In related embodiments the effective amount of isoproterenol HCl is approximately 0.0001 mg/kg, 0.0005 mg/kg, 0.001 mg/kg, 0.005 mg/kg, 0.01 mg/kg, 0.05 mg/kg, 0.1 mg/kg, 0.5 mg/kg, 1.0 mg/kg, 10 mg/kg, 20 mg/kg, 30 mg/kg, 40 mg/kg, 50 mg/kg, 60 mg/kg, 70 mg/kg, 80 mg/kg, 90 mg/kg, 100 mg/kg, 110 mg/kg, 120 mg/kg, 130 mg/kg, 140 mg/kg, or 150 mg/kg of patient body weight. In related embodiments the effective amount of isoproterenol HCl is about 0.0001 mg/kg to 0.001 mg/kg, 0.01 mg/kg to 0.1 mg/kg, 1.0 mg/kg to 20 mg/kg, 40 mg/kg to 60 mg/kg, 80 mg/kg to 100 mg/kg, or 120 mg/kg to 140 mg/kg of patient body weight. In related embodiments the effective amount of isoproterenol HCl is about 0.0005 mg/kg to 0.005 mg/kg, 0.05 mg/kg to 0.1 mg/kg, 0.5 mg/kg to 10 mg/kg, 30 mg/kg to 50 mg/kg, 70 mg/kg to 90 mg/kg, 110 mg/kg to 130 mg/kg, or 130 mg/kg to 150 mg/kg of patient body weight.

In one embodiment, the composition topically administered to a patient in the methods of the invention comprises an effective amount of the vasoconstrictor norepinephrine in a concentration in the range of about 0.00001 mg/kg of patient body weight to about 2 mg/kg of patient body weight. For adults the preferred norepinephrine concentration range is about 0.0001 mg/kg to about 0.01 mg/kg. In related embodiments the effective amount of norepinephrine is approximately 0.0001 mg/kg, 0.0005 mg/kg, 0.001 mg/kg, 0.005 mg/kg, 0.01 mg/kg, 0.05 mg/kg, 0.1 mg/kg, 0.5 mg/kg, 1.0 mg/kg, 1.5 mg/kg, or 2 mg/kg of patient body weight. In related embodiments the effective amount of norepinephrine is about 0.0001 mg/kg to 0.001 mg/kg, 0.01 mg/kg to 0.1 mg/kg, or 1.0 mg/kg to 2 mg/kg of patient body weight. In related embodiments the effective amount of norepinephrine is about 0.0005 mg/kg to 0.005 mg/kg, 0.05 mg/kg to 0.5 mg/kg, or 1.5 mg/kg to 2 mg/kg of patient body weight.

In one embodiment, the composition topically administered to a patient in the methods of the invention comprises an effective amount of the vasoconstrictor Serotonin™ in a concentration in the range of about 0.0001 mg/kg of patient body weight to about 750 mg/kg of patient body weight. For adults the preferred Serotonin™ concentration range is about 0.001 mg/kg to about 0.6 mg/kg. In related embodiments the effective amount of Serotonin™ is approximately 0.001 mg/kg, 0.005 mg/kg, 0.01 mg/kg, 0.05 mg/kg, 0.1 mg/kg, 0.5 mg/kg, 1.0 mg/kg, 10 mg/kg, 20 mg/kg, 30 mg/kg, 40 mg/kg, 50 mg/kg, 60 mg/kg, 70 mg/kg, 80 mg/kg, 90 mg/kg, 100 mg/kg, 110 mg/kg, 120 mg/kg, 130 mg/kg, 140 mg/kg, 150 mg/kg, 160 mg/kg, 170 mg/kg, 180 mg/kg, 190 mg/kg, 200 mg/kg, 210 mg/kg, 250 mg/kg, 300 mg/kg, 350 mg/kg, 400 mg/kg, 450 mg/kg, 500 mg/kg, 550 mg/kg, 600 mg/kg, 650 mg/kg, 700 mg/kg, or 750 mg/kg of patient body weight. In related embodiments the effective amount of Serotonin™ is about 0.001 mg/kg to 0.01 mg/kg, 0.1 mg/kg to 1.0 mg/kg, 20 mg/kg to 40 mg/kg, 60 mg/kg to 80 mg/kg, 100 mg/kg to 120 mg/kg, 140 mg/kg to 160 mg/kg, 180 mg/kg to 200 mg/kg, 210 mg/kg to 300 mg/kg, 400 mg/kg to 500 mg/kg, or 600 mg/kg to 700 mg/kg of patient body weight. In related embodiments the effective amount of Serotonin™ is about 0.005 mg/kg to 0.05 mg/kg, 0.5 mg/kg to 10 mg/kg, 30 mg/kg to 50 mg/kg, 70 mg/kg to 90 mg/kg, 110 mg/kg to 130 mg/kg, 150 mg/kg to 170 mg/kg, 190 mg/kg to 210 mg/kg, 250 mg/kg to 350 mg/kg, 450 mg/kg to 550 mg/kg, or 650 mg/kg to 750 mg/kg of patient body weight.

In one embodiment, the composition topically administered to a patient in the methods of the invention comprises an effective amount of the vasoconstrictor endothelin in a concentration in the range of about $4.5 \times 10^{-8}$ mg/kg of patient body weight to about $5.0 \times 10^{-6}$ mg/kg of patient body weight. In related embodiments the effective amount of endothelin is approximately $4.5 \times 10^{-8}$ mg/kg, $5.0 \times 10^{-8}$ mg/kg, $5.5 \times 10^{8}$ mg/kg, $6.0 \times 10^{-8}$ mg/kg, $6.5 \times 10^{-8}$ mg/kg, $7.0 \times 10^{-8}$ mg/kg, $7.5 \times 10^{8}$ mg/kg, $8.0 \times 10^{-8}$ mg/kg, $8.5 \times 10^{-8}$ mg/kg, $9.0 \times 10^{-8}$ mg/kg, $9.5 \times 10^{-8}$ mg/kg, $1.0 \times 10^{-7}$ mg/kg, $1.5 \times 10^{-7}$ mg/kg, $2.0 \times 10^{-7}$ mg/kg, $2.5 \times 10^{-7}$ mg/kg, $3.0 \times 10^{-7}$ mg/kg, $3.5 \times 10^{-7}$ mg/kg, $4.0 \times 10^{-7}$ mg/kg, $4.5 \times 10^{-7}$ mg/kg, $5.0 \times 10^{-7}$ mg/kg, $5.5 \times 10^{-7}$ mg/kg, $6.0 \times 10^{-7}$ mg/kg, $6.5 \times 10^{-7}$ mg/kg, $7.0 \times 10^{-7}$ mg/kg, $7.5 \times 10^{-7}$ mg/kg, $8.0 \times 10^{-7}$ mg/kg, $8.5 \times 10^{-7}$ mg/kg, $9.0 \times 10^{-7}$ mg/kg, $1.0 \times 10^{-6}$ mg/kg, $1.5 \times 10^{-6}$ mg/kg, $2.0 \times 10^{-6}$ mg/kg, $2.5 \times 10^{-6}$ mg/kg, $3.0 \times 10^{-6}$ mg/kg, $3.5 \times 10^{-6}$ mg/kg, $4.0 \times 10^{-6}$ mg/kg, $4.5 \times 10^{-6}$ mg/kg, or $5.0 \times 10^{-6}$ mg/kg of patient body weight. In related embodiments the effective amount of endothelin is about $5.0 \times 10^{-8}$ mg/kg to $6.0 \times 10^{-8}$ mg/kg, $7.0 \times 10^{-8}$ mg/kg to $8.0 \times 10^{-8}$ mg/kg, $9.0 \times 10^{-8}$ mg/kg to $1.0 \times 10^{-7}$ mg/kg, $2.0 \times 10^{-7}$ mg/kg to $3.0 \times 10^{-7}$ mg/kg, $4.0 \times 10^{-7}$ mg/kg to $5.0 \times 10^{-7}$ mg/kg, $6.0 \times 10^{-7}$ mg/kg to $7.0 \times 10^{-7}$ mg/kg, $8.0 \times 10^{-7}$ mg/kg to $9.0 \times 10^{-7}$ mg/kg, $1.0 \times 10^{-6}$ mg/kg to $2.0 \times 10^{-6}$ mg/kg, $3.0 \times 10^{-6}$ mg/kg to $4.0 \times 10^{-6}$ mg/kg, or $4.0 \times 10^{-6}$ mg/kg to $5.0 \times 10^{-6}$ mg/kg of patient body weight. In related embodiments the effective amount of endothelin is about $4.5 \times 10^{-8}$ mg/kg to $5.5 \times 10^{-8}$ mg/kg, $6.5 \times 10^{-8}$ mg/kg to $7.5 \times 10^{-8}$ mg/kg, $8.5 \times 10^{-8}$ mg/kg to $9.5 \times 10^{-8}$ mg/kg, $1.5 \times 10^{-7}$ mg/kg to $2.5 \times 10^{-7}$ mg/kg, $3.5 \times 10^{-7}$ mg/kg to $4.5 \times 10^{-7}$ mg/kg, $5.5 \times 10^{-7}$ mg/kg to $6.5 \times 10^{-7}$ mg/kg, $7.5 \times 10^{-7}$ mg/kg to $8.5-10^{-7}$ mg/kg, $1.5 \times 10^{-6}$ mg/kg to $2.5 \times 10^{-6}$ mg/kg, or $3.5 \times 10^{-6}$ mg/kg to $4.5 \times 10^{-6}$ mg/kg of patient body weight.

For other vasoconstrictors, including but not limited to, endothelin-1, epinephrine, phenylephrine, thromboxane, prostaglandin, methergine, oxytocin, isopreland U-46619, papaverine, yohimbine, visnadin, khellin, bebellin, and nicotinate derivatives, one skilled in the art would be able to determine appropriate effective doses using the methods described in sections 5.2 and 5.4. In related embodiments the effective amount of a vasoconstrictor is approximately $4.5 \times 10^{-8}$ mg/kg, $5.0 \times 10^{-8}$ mg/kg, $6.0 \times 10^{-8}$ mg/kg, $7.0 \times 10^{-8}$ mg/kg, $8.0 \times 10^{-8}$ mg/kg, $9.0 \times 10^{-8}$ mg/kg, $1.0 \times 10^{-7}$ mg/kg, $2.0 \times 10^{-7}$ mg/kg, $3.0 \times 10^{-7}$ mg/kg, $4.0 \times 10^{-7}$ mg/kg, $5.0 \times 10^{-7}$ mg/kg, $6.0 \times 10^{-7}$ mg/kg, $7.0 \times 10^{-7}$ mg/kg, $8.0 \times 10^{-7}$ mg/kg, $9.0 \times 10^{-7}$ mg/kg, $1.0 \times 10^{-6}$ mg/kg, $2.0 \times 10^{-6}$ mg/kg, $3.0 \times 10^{-6}$ mg/kg, $4.0 \times 10^{-6}$ mg/kg, $5.0 \times 10^{-6}$ mg/kg, $6.0 \times 10^{-6}$ mg/kg, $7.0 \times 10^{-6}$ mg/kg, $8.0 \times 10^{-6}$ mg/kg, $9.0 \times 10^{-6}$ mg/kg, $1.0 \times 10^{-5}$ mg/kg, $2.0 \times 10^{-5}$ mg/kg, $3.0 \times 10^{-5}$ mg/kg, $4.0 \times 10^{-5}$ mg/kg, $5.0 \times 10^{-5}$ mg/kg, $6.0 \times 10^{-5}$ mg/kg, $7.0 \times 10^{-5}$ mg/kg, $8.0 \times 10^{-5}$ mg/kg, $9.0 \times 10^{-5}$ mg/kg, $1.0 \times 10^{-4}$ mg/kg, $2.0 \times 10^{-4}$ mg/kg, $3.0 \times 10^{-4}$ mg/kg, $4.0 \times 10^{-4}$ mg/kg, $5.0 \times 10^{-4}$ mg/kg, $6.0 \times 10^{-4}$ mg/kg, $7.0 \times 10^{-4}$ mg/kg, $8.0 \times 10^{-4}$ mg/kg, $9.0 \times 10^{-4}$ mg/kg, $1.0 \times 10^{-3}$ mg/kg, $2.0 \times 10^{-3}$ mg/kg, $3.0 \times 10^{-3}$ mg/kg, $4.0 \times 10^{-3}$ mg/kg, $5.0 \times 10^{-3}$ mg/kg, $6.0 \times 10^{-3}$ mg/kg, $7.0 \times 10^{-3}$ mg/kg, $8.0 \times 10^{-3}$ mg/kg, $9.0 \times 10^{-3}$ mg/kg, $1.0 \times 10^{-2}$ mg/kg, $2.0 \times 10^{-2}$ mg/kg, $3.0 \times 10^{-2}$ mg/kg, $4.0 \times 10^{-2}$ mg/kg, $5.0 \times 10^{-2}$ mg/kg, $6.0 \times 10^{-2}$ mg/kg, $7.0 \times 10^{-2}$ mg/kg, $8.0 \times 10^{-2}$ mg/kg, $9.0 \times 10^{-2}$ mg/kg, 0.1 mg/kg, 0.5 mg/kg, 1.0 mg/kg, 10 mg/kg, 20 mg/kg, 30 mg/kg, 40 mg/kg, 50 mg/kg, 60 mg/kg, 70 mg/kg, 80 mg/kg, 90 mg/kg, 100 mg/kg, 110 mg/kg, 120 mg/kg, 130 mg/kg, 140 mg/kg, 150 mg/kg, 160 mg/kg, 170 mg/kg, 180 mg/kg, 190 mg/kg, 200 mg/kg, 210 mg/kg, 250 mg/kg, 300 mg/kg, 350 mg/kg, 400 mg/kg, 450 mg/kg, 500 mg/kg, 550 mg/kg, 600 mg/kg, 650 mg/kg, 700 mg/kg, 750 mg/kg, 800 mg/kg, 850 mg/kg, 900 mg/kg, 950 mg/kg, 1000 mg/kg, 1100 mg/kg, 1200 mg/kg, 1300 mg/kg, 1400 mg/kg, or 1500 mg/kg of patient body weight.

In certain embodiments, the effective amount of a vasoconstrictor is in the range of about $6.0 \times 10^{-8}$ mg/kg to $1.0 \times 10^{-7}$ mg/kg, $1.0 \times 10^{-7}$ mg/kg to $4.0 \times 10^{-7}$ mg/kg, $4.0 \times 10^{-7}$ mg/kg to $8.0 \times 10^{-7}$ mg/kg, $8.0 \times 10^{-7}$ mg/kg to $2.0 \times 10^{-6}$ mg/kg, $2.0 \times 10^{-6}$ mg/kg to $6.0 \times 10^{-6}$ mg/kg, $6.0 \times 10^{-6}$ mg/kg to $1.0 \times 10^{-5}$ mg/kg, $1.0 \times 10^{-5}$ mg/kg to $4.0 \times 10^{-5}$ mg/kg, $4.0 \times 10^{-5}$ mg/kg to $8.0 \times 10^{-5}$ mg/kg, $8.0 \times 10^{-5}$ mg/kg to $2.0 \times 10^{-4}$ mg/kg, $2.0 \times 10^{-4}$ mg/kg to $6.0 \times 10^{-4}$ mg/kg, $6.0 \times 10^{-4}$ mg/kg to $1.0 \times 10^{-3}$ mg/kg, $1.0 \times 10^{-3}$ mg/kg to $4.0 \times 10^{-3}$ mg/kg, $4.0 \times 10^{-3}$ mg/kg to $8.0 \times 10^{-3}$ mg/kg, $8.0 \times 10^{-3}$ mg/kg to $2.0 \times 10^{-2}$ mg/kg, $2.0 \times 10^{-2}$ mg/kg to $6.0 \times 10^{-2}$ mg/kg, $6.0 \times 10^{-2}$ mg/kg to 0.1 mg/kg, 0.1 mg/kg to 0.4 mg/kg, 0.4 mg/kg to 0.8 mg/kg, 0.8 mg/kg to 2.0 mg/kg, 2.0 mg/kg to 6.0 mg/kg, 6.0 mg/kg to 10 mg/kg, 10 mg/kg to 40 mg/kg, 40 mg/kg to 80 mg/kg, 80 mg/kg to 120 mg/kg, 120 mg/kg to 160 mg/kg, 160 mg/kg to 200 mg/kg, 200 mg/kg to 240 mg/kg, 280 mg/kg to 320 mg/kg, 320 mg/kg to 360 mg/kg, 360 mg/kg to 400 mg/kg, 400 mg/kg to 440 mg/kg, 440 mg/kg to 480 mg/kg, 480 mg/kg to 520 mg/kg, 520 mg/kg to 560 mg/kg, 560 mg/kg to 600 mg/kg, 600 mg/kg to 640 mg/kg, 640 mg/kg to 680 mg/kg, 680 mg/kg to 720 mg/kg, 720 mg/kg to 760 mg/kg, 760 mg/kg to 800 mg/kg, 800 mg/kg to 840 mg/kg, 840 mg/kg to 880 mg/kg, 880 mg/kg to 920 mg/kg, 920 mg/kg to 960 mg/kg, 960 mg/kg to 1000 mg/kg, 1000 mg/kg to 1040 mg/kg, 1040 mg/kg to 1080 mg/kg, 1080 mg/kg to 1120 mg/kg, 1120 mg/kg to 1160 mg/kg, 1160 mg/kg to 1200 mg/kg, 1200 mg/kg to 1240 mg/kg, 1240 mg/kg to 1280 mg/kg, 1280 mg/kg to 1320 mg/kg, 1320 mg/kg to 1360 mg/kg, 1360 mg/kg to 1400 mg/kg, 1400 mg/kg to 1440 mg/kg, 1440 mg/kg to 1480 mg/kg, or 1480 mg/kg to 1520 mg/kg of patient body weight.

In certain embodiments, the effective amount of a vasoconstrictor is in the range of about $4.5 \times 10^{-8}$ mg/kg to $8.0 \times 10^{-8}$ mg/kg, $8.0 \times 10^{-8}$ mg/kg to $2.0 \times 10^{-7}$ mg/kg, $2.0 \times 10^{-7}$ mg/kg to $6.0 \times 10^{-7}$ mg/kg, $6.0 \times 10^{-7}$ mg/kg to $1.0 \times 10^{-6}$ mg/kg, $1.0 \times 10^{-6}$ mg/kg to $4.0 \times 10^{-6}$ mg/kg, $4.0 \times 10^{-6}$ mg/kg to $8.0 \times 10^{-6}$ mg/kg, $8.0 \times 10^{-6}$ mg/kg to $2.0 \times 10^{-5}$ mg/kg, $2.0 \times 10^{-5}$ mg/kg to $6.0 \times 10^{-5}$ mg/kg, $6.0 \times 10^{-5}$ mg/kg to $1.0 \times 10^{-4}$ mg/kg, $1.0 \times 10^{-4}$ mg/kg to $4.0 \times 10^{-4}$ mg/kg, $4.0 \times 10^{-4}$ mg/kg to $8.0 \times 10^{-4}$ mg/kg, $8.0 \times 10^{-4}$ mg/kg to $2.0 \times 10^{-3}$ mg/kg, $2.0 \times 10^{-3}$ mg/kg to $6.0 \times 10^{-3}$ mg/kg, $6.0 \times 10^{-3}$ mg/kg to $1.0 \times 10^{-2}$ mg/kg, $1.0 \times 10^{-2}$ mg/kg to $4.0 \times 10^{-2}$ mg/kg, $4.0 \times 10^{-2}$ mg/kg to $8.0 \times 10^{-2}$ mg/kg, $8.0 \times 10^{-2}$ mg/kg to 0.2 mg/kg, 0.2 mg/kg to 0.6 mg/kg, 0.6 mg/kg to 1.0 mg/kg, 1.0 mg/kg to 4.0 mg/kg, 4.0 mg/kg to 8.0 mg/kg, 8.0 mg/kg to 12 mg/kg, 12 mg/kg to 16 mg/kg, 16 mg/kg to 20 mg/kg, 20 mg/kg to 60 mg/kg, 60 mg/kg to 100 mg/kg, 100 mg/kg to 140 mg/kg, 140 mg/kg to 180 mg/kg, 180 mg/kg to 220 mg/kg, 220 mg/kg to 260 mg/kg, 260 mg/kg to 300 mg/kg, 300 mg/kg to 340 mg/kg, 340 mg/kg to 380 mg/kg, 380 mg/kg to 420 mg/kg, 420 mg/kg to 460 mg/kg, 460 mg/kg to 500 mg/kg, 500 mg/kg to 540 mg/kg, 540 mg/kg to 580 mg/kg, 580 mg/kg to 620 mg/kg, 620 mg/kg to 660 mg/kg, 660 mg/kg to 700 mg/kg, 700 mg/kg to 740 mg/kg, 740 mg/kg to 780 mg/kg, 780 mg/kg to 820 mg/kg, 820 mg/kg to 860 mg/kg, 860 mg/kg to 900 mg/kg, 900 mg/kg to 940 mg/kg, 940 mg/kg to 980 mg/kg, 980 mg/kg to 1020 mg/kg, 1020 mg/kg to 1060 mg/kg, 1060 mg/kg to 1100 mg/kg, 1100 mg/kg to 1140 mg/kg, 1140 mg/kg to 1180 mg/kg, 1180 mg/kg to 1220 mg/kg, 1220 mg/kg to 1260 mg/kg, 1260 mg/kg to 1300 mg/kg, 1300 mg/kg to 1340 mg/kg, 1340 mg/kg to 1380 mg/kg, 1380 mg/kg to 1420 mg/kg, 1420 mg/kg to 1460 mg/kg, or 1460 mg/kg to 1500 mg/kg of patient body weight.

In general, the effective does of a vasoconstrictor used in the compositions of the methods, compositions, and kits of the invention is a concentration that is less than an amount that would cause systemic vasoconstriction when administered intravenously and greater than an amount that would have only a localized effect when applied to the skin surface rather than effecting a breach or puncture in a vein or artery.

The effective amount of a vasoconstrictor can also be described in the context of particular formulations of the compositions used in the methods, compositions, and kits of the invention. For example, where the composition is formulated as or applied to a patch for administration following a cardiac catheterization procedure, adrenaline is the vasoconstrictor used in the composition, and the patient is an adult weighing about 70 kg, then the patch should comprise adrenaline in the concentration range of about 0.00075 mg/kg to about 37.5 mg/kg. Since a patch used in such procedures is typically about 4 cm² to 25 cm², depending on the F size of the catheter used, one skilled in the art could readily determine the concentration in units of mg of adrenaline per cm² of patch, e.g., about 0.00020 mg/cm² to about 1.5 mg/cm². Similarly, for example, where the composition is formulated as a gel or liquid, for administration following a cardiac catheterization procedure, adrenaline is the vasoconstrictor used in the composition, and the patient is an adult weighing about 70 kg, then the gel should comprise adrenaline in the concentration range of about 0.00075 mg/kg to about 37.5 mg/kg. Since a gel used in such procedures is typically about 1-2 ml, one skilled in the art could readily determine the concentration in units of mg of adrenaline per ml of gel, e.g., about 0.00075 mg/ml to about 18.75 mg/ml.

The example conversion calculation described above can be performed to allow the extrapolation of suitable concentration ranges for topical application any of the dosage ranges for any of the vasoconstrictors and/or coagulants described herein above or any vasoconstrictors and/or coagulant suitable for use in the methods, compositions, and kits of the invention. In preferred embodiments, where the composition is formulated as a patch, gel, or liquid, such compositions can be manufactured for general use for adults, e.g., adults weighing about 50, 60, 70, 80, or 90 kg, and a topical administration area, e.g., of a patch, of about 1-2, 2-4, 4-8, 8-12, 12-15, 15-20, 20-25, or 25-30 cm², or a topical administration volume, e.g., of a liquid or gel, of about 0.25-0.5, 0.5-1, 1-1.25, 1.25-1.5, 1.5-1.75, 1.75-2, 2-2.5, or 2.5-3 ml.

5.5 Kits

A kit is also provided which according to the invention comprises any of the above described embodiments. The kit can include the composition contained within a sealed, water proof, sterile package which facilitates removal of the composition without contamination. Materials from which containers may be made include aluminum foil, plastic, or another conventional material that is easily sterilized. The kit can contain a single composition or multiple compositions, preferably wherein each is provided in a separate, waterproof, sterile package.

In another embodiment, a container having dual compartments is provided. A first compartment contains the composition, while the second compartment contains a topical barrier, membrane, or film according to the invention. In field use, the barrier, membrane, or film can be readily dipped into an opened first compartment ans subsequently applied to the wound. The composition can be applied or added to a topical barrier, membrane, or film prior to being packaged and sterilized or the composition can be formulated as a barrier, membrane, or film. In another embodiment, the kit may not contain a barrier, membrane, or film if the composition is not formulated as such.

According to one aspect of the invention, various specialized kits can be provided. The kit can contain multiple compositions of the invention, wherein each is contained within a separate sealed sterile package or container. The kit can contain in one or more containers, a an effective amount of a vasoconstrictor, wherein the vasoconstrictor does not comprise a poly-β-1→4 N-acetylglucosamine polymer or derivative thereof, while in another separate container a pharmaceutically acceptable carrier can be packaged. In a separate container the kit can contain a neutral liquid, neutral gel or neutral solid. The kit may also contain a coagulant in accord with the composition of the invention as described herein.

The kit can comprise a composition that can be formulated as a barrier-forming material that forms a barrier to blood. The kit can comprise a composition that can coat, be added to, or integrated into a barrier-forming material that forms a barrier to blood. In one embodiment a kit comprises a pharmaceutical composition comprising a patch made of barrier-forming materials that are embedded with one or more coagulant and/or vasoconstrictor agent(s). In one embodiment a kit comprises a pharmaceutical composition comprising a gauze embedded with one or more coagulant and/or vasoconstrictor agent(s). In certain embodiments, a kit comprises pharmaceutical compositions comprising a barrier-forming material embedded or combined with one or more coagulant and/or vasoconstrictor agent(s), wherein the barrier-forming material contains an adhesive so that the material can be adhere to a patient's skin surface. Alternatively, a kit lacks barrier-forming materials.

A kit can comprise a notice regarding FDA approval and/or instructions for use at a distance and/or in combination with compression.

A kit may be prescribed, for example, to patients requiring anticoagulant therapy, to avert the risk of serious bleeding which can occur from minor injury. A kit may be used, for example, to treat a breach or puncture in a vein or artery resulting from catheterization. In one embodiment a kit comprises a patch embedded or coated with a vasoconstrictor, a coagulant, or an agent that functions as both a vasoconstrictor or coagulant. In another embodiment a kit comprises a gel that can be used in the methods of the invention, wherein the gel comprises a vasoconstrictor, a coagulant, or an agent that functions as both a vasoconstrictor or coagulant.

Additionally, a kit designed for emergency or military use can also contain disposable pre-sterilized instruments, such as scissors, scalpel, clamp, tourniquet, elastic or inelastic bandages, or the like. In a preferred embodiment the kit contains gauze.

6. EXAMPLE 1

Determining Rate of Cessation or Time to Achieve Cessation of Blood Flow

This blinded, randomized, placebo controlled trial is designed to examine an arterial puncture of a femoral artery in dogs intended to simulate cardiac catheterization. This method takes into consideration differences in bleeding time and the amount of compression applied.

6.1 Materials and Methods

Dogs are randomly assigned to have either compression in conjunction with a topical barrier-forming material without a vasoconstrictor or coagulant or a barrier-forming material coated with or formulated from the composition of the invention in conjunction with compression.

In preferred embodiments, the animal model provides a control. For example, in dogs the femoral arteries in each hind leg can be punctured in an identical manner to create comparable punctures and the treatment being tested can be applied to one puncture while the other is left untreated or receives compression alone.

A mechanical pressure clamp is applied over the barrier-forming material. At 5 minute intervals, the clamp is loosened to check for blood flow from the wound site, but the barrier-forming material is not disturbed. If blood continues to flow from the wound, the clamp is re-applied until bleeding completely stops, with checks performed every five minutes. A fluid-filled balloon connected to a pressure transducer is used to measure the amount of pressure applied. A pre-procedure bleeding time is also preformed.

By comparing pre-procedure bleeding variables such as pre-procedure hematocrit (%) and bleeding time (mins), for each group differences in bleeding can be eliminated through selection of particular animals, or compensated for by calculating the rate of cessation or time to achieve cessation of bleeding from a base values.

Clamp pressure applied to the femoral arterial puncture site can be carefully controlled and recorded for each dog, allowing calculation of a mean clamp pressure (mmHg) for both the placebo group and the group receiving the composition of the invention.

The superficial nature of the femoral artery in dogs allows for direct and consistent visualization of hematoma formation. Visualization can be by any of the methods described herein such as ultrasonography, or scintigraphic imaging. External signs are also indicative of hematoma formation, including ecchymosis (blue or purplish skin discoloration greater than or equal to 2.5 cm in diameter), swelling (greater than or equal to 2.5 cm in diameter and 0.5 cm in height). The cannula can also be removed from the dogs following application of the methods of the invention to determine frequency of hematomas or other vascular complications.

Percent differences between mean values for each treatment group are calculated for several variables including, pre-procedure hematocrit (%), pre-procedure bleeding time (mins), time to cessation of bleeding from the puncture site (mins), the mean numbers of hematomas, and mean clamp pressure (mmHg). The statistical significance (P values) of the differences between the mean values for each variable are calculated by standard statistical methods.

The present invention is not to be limited in scope by the specific embodiments described herein. Indeed, various modifications of the invention in addition to those described will become apparent to those skilled in the art from the foregoing description and accompanying figures. Such modifications are intended to fall within the scope of the appended claims.

Various publications are cited herein, the disclosures of which are incorporated by reference in their entireties.

The present invention is not to be limited in scope by the specific embodiments described herein. Indeed, various modifications of the invention in addition to those described will become apparent to those skilled in the art from the foregoing description and accompanying figures. Such modifications are intended to fall within the scope of the appended claims.

Various publications are cited herein, the disclosures of which are incorporated by reference in their entireties.

The invention can be illustrated by the following embodiments enumerated in the numbered paragraphs that follow:

1. A method for treating a breach or puncture in a vein or artery of a patient, comprising:
    a) applying topically to the patient's skin over a wound contiguous with the breach or puncture in the vein or artery a composition comprising an effective amount of a vasoconstrictor, wherein the vasoconstrictor does not comprise a poly-$\beta$-1→4 N-acetylglucosamine polymer or derivative thereof; and concurrently
    b) applying compression to the breached or punctured vein or artery,
    wherein a cessation or reduction of blood flow out of the breach or puncture in the vein or artery is achieved at a greater rate or in less time than applying compression in conjunction with a topical barrier-forming material without the vasoconstrictor.
2. A method for achieving a cessation of blood flow or sealing of a breach or puncture in a vein or artery and a cessation of blood flow or sealing of a skin surface wound that is contiguous with the breach or puncture comprising:
    a) applying topically to the patient's skin over a wound contiguous with a breach or puncture in a vein or artery a composition comprising a vasoconstrictor or coagulant, wherein the vasoconstrictor or coagulant does not comprise a poly-$\beta$-1→4 N-acetylglucosamine polymer or derivative thereof;
    b) concurrently applying compression to the breached or punctured vein or artery; and
    c) recording the amount of blood flow from the wound and the puncture, wherein an amount of the vasoconstrictor or coagulant is effective to increase sealing or decrease cessation of blood flow from the breach or puncture in the vein or artery and increase sealing or decrease cessation of blood flow from the skin surface wound, in comparison to applying compression in conjunction with a topical barrier-forming material without the vasoconstrictor.

3. A method for treating a breach or puncture in a vein or artery of a patient, comprising:
   a) applying topically to the patient's skin over a wound contiguous with the breach or puncture in the vein or artery a composition comprising an effective amount of a coagulant, wherein the coagulant does not comprise a poly-β-1→4 N-acetylglucosamine polymer or derivative thereof; and concurrently
   b) applying compression to the breached or punctured vein or artery,
   wherein a cessation or reduction of blood flow out of the breach or puncture in the vein or artery is achieved at a greater rate in less time than applying compression in conjunction with a topical barrier-forming material without a coagulant.

4. A method for treating a breach or puncture in a vein or artery of a patient, comprising:
   a) applying topically to the patient's skin over a wound contiguous with the breach or puncture in the vein or artery a composition comprising an effective amount of a vasoconstrictor and a coagulant, wherein the vasoconstrictor and the coagulant do not comprise a poly-β-1→4 N-acetylglucosamine polymer or derivative thereof; and concurrently
   b) applying compression to the breached or punctured vein or artery,
   wherein a cessation or reduction of blood flow out of the breach or puncture in the vein or artery is achieved at a greater rate or in less time than applying compression in conjunction with a topical barrier-forming material without the vasoconstrictor and the coagulant.

5. The method of any one of paragraphs 1-4, wherein the composition further comprises an anti-fungal or antibacterial agent.

6. The method of any one of paragraphs 1-4, wherein the composition further comprises collagen.

7. The method of any one of paragraphs 1-4, wherein the composition further comprises a pharmaceutical carrier.

8. The method of any one of paragraphs 1-4, wherein the composition is formulated as a gel, solid, liquid, sponge, foam, spray, emulsion, suspension, or solution.

9. The method of any one of paragraphs 1-4, wherein the composition further comprises a neutral liquid, neutral gel or neutral solid.

10. The method of paragraph 9, wherein the composition further comprises a neutral solid and wherein the neutral solid is a gauze.

11. The method of paragraph 8, wherein the composition is in the form of a coating on a neutral solid.

12. The method of paragraph 11, wherein the neutral solid is a gauze.

13. The method of any one of paragraphs 1-4, wherein the barrier-forming material is a gauze.

14. The method of any one of paragraphs 2, 3, or 4, wherein the coagulant is selected from the group consisting of alpha-2-antiplasmin, alpha-1-antitrypsin, alpha-2-macroglobulin, aminohexanoic acid, aprotinin, a source of Calcium ions, calcium alginate, calcium-sodium alginate, casein Kinase II, chitin, chitosan, collagen, cyanoacrylates, epsilon-aminocaproic acid, Factor XIII, fibrin, fibrin glue, fibrinogen, fibronectin, gelatin, living platelets, methacrylates, PAI-1, PAI-2, plasmin activator inhibitor, plasminogen, platelet agonists, protamine sulfate, prothrombin, an RGD peptide, sphingosine, a sphingosine derivative, thrombin, thromboplastin, and tranexamic acid.

15. The method of any one of paragraphs 1 or 4, wherein the vasoconstrictor is selected from the group consisting of adrenaline, endothelin-1, epinephrine, phenylephrine, serotonin, thromboxane, and U-46619.

16. The method of any one of paragraphs 1-4, wherein the patient is a human.

17. The method of any one of paragraphs 1-4, wherein composition applied is a film or membrane.

18. The method of paragraph 17, wherein the film or membrane comprises a barrier-forming material.

19. The method of any one of paragraphs 1-4, wherein composition is formulated as a mat, string, microbead, microsphere, or microfibril.

20. The method of any one of paragraphs 1-4, wherein the composition further comprises a biodegradable material.

21. The method of paragraph 20, wherein the biodegradable material is selected from the group consisting of a polyanionic polysaccharide, alginic acid, collagen, a polypeptide, a polyglycolide, a polylactide, a polycaprolactone, dextran and a copolymer of dextran, a polyglycolide, a polylactide, a polydioxanone, a polyestercarbonate, a polyhydroxyalkonate, and a polycaprolactone and a copolymer thereof.

22. The method of any one of paragraphs 1-4, further comprising before step (a) the step of administering to the patient an anticoagulant.

23. The method of paragraph 22, wherein the anticoagulant is selected from the group consisting of coumadin, heparin, nadroparin, asparin, and a thrombolytic agent.

24. The method of paragraph 23, wherein the composition further comprises protamine sulfate in an amount effective to neutralize heparin.

25. The method of any one of paragraphs 1-4, wherein the artery is the femoral, radial, brachial, or axillary artery.

26. The method of any one of paragraphs 1-4, wherein the vein is the femoral, internal jugular, or subclavian vein.

27. The method of any one of paragraphs 1-4, wherein the compression is manual compression.

28. The method of any one of paragraphs 1-4, wherein the compression is mechanical compression.

29. The method of any one of paragraphs 1-4, wherein the compression is applied to the vein or artery proximal of the puncture or breach.

30. The method of any one of paragraphs 1-4, wherein the compression is applied at the site of application of the composition.

31. The method of any one of paragraphs 1-4, wherein the compression is applied with a compression bandage.

32. The method of any one of paragraphs 1-4, further comprising, repeating step (b).

33. The method of paragraph 32, wherein the rate is at least 10% greater than applying compression in conjunction with a topical barrier-forming material without a vasoconstrictor.

34. The method of paragraph 32, wherein the rate is at least 20% greater than applying compression in conjunction with a topical barrier-forming material without a vasoconstrictor.

35. The method of paragraph 32, wherein the rate is at least 30% greater than applying compression in conjunction with a topical barrier-forming material without a vasoconstrictor.

36. The method of paragraph 32, wherein the rate is at least 40% greater than applying compression in conjunction with a topical barrier-forming material without a vasoconstrictor.

37. The method of paragraph 32, wherein the rate is at least 50% greater than applying compression in conjunction with a topical barrier-forming material without a vasoconstrictor.

38. The method of any one of paragraphs 1-4, wherein the vein or artery is breached or punctured by a catheter.

39. The method of any one of paragraphs 1-4, wherein the skin wound contiguous with the breach or puncture in the vein or artery is 10, 9, 8, 7, 6, 5, or 4 cm from the puncture in the vein or artery.

40. A method for decreasing the occurrence of localized vascular complications comprising:
    a) applying topically to the patient's skin over a wound contiguous with a breach or puncture in a vein or artery a composition comprising a vasoconstrictor or coagulant, wherein the vasoconstrictor or coagulant does not comprise a poly-β-1→4 N-acetylglucosamine polymer or derivative thereof;
    b) concurrently applying compression to the breached or punctured vein or artery; and
    c) recording the occurrence of localized vascular complications,
    wherein an amount of the vasoconstrictor or coagulant is effective to cause sealing of the breach or puncture in the vein or artery, reducing the rate of localized vascular complications in comparison to applying compression in conjunction with a topical barrier-forming material without a vasoconstrictor.

41. The method of paragraph 40, wherein the rate is 50% less than applying compression in conjunction with a topical barrier without a vasoconstrictor.

42. The method of paragraph 40, wherein the vein or artery is breached or punctured by a catheter.

43. A pharmaceutical composition for topically treating a breach or puncture in a vein or artery, comprising:
    a) an effective amount of a vasoconstrictor, wherein the vasoconstrictor does not comprise a poly-β-1→4 N-acetylglucosamine polymer or derivative thereof; and
    b) a pharmaceutically acceptable carrier.

44. The pharmaceutical composition of paragraph 43, wherein the composition further comprises a coagulant.

45. The pharmaceutical composition of paragraphs 43 or 44, further comprising a neutral liquid, neutral gel or neutral solid.

46. The pharmaceutical composition of paragraph 45, wherein the composition further comprises a neutral solid and wherein the neutral solid is a gauze.

47. A kit comprising in one or more containers a composition comprising:
    a) an effective amount of a vasoconstrictor, wherein the vasoconstrictor does not comprise a poly-β-1→4 N-acetylglucosamine polymer or derivative thereof; and
    b) a pharmaceutically acceptable carrier,
and instructions for topically treating a breach or puncture in a vein or artery.

48. The kit of paragraph 47, wherein the composition further comprises a coagulant.

49. The kit of paragraph 47, further comprising a neutral liquid, neutral gel or neutral solid.

50. The kit of paragraph 49, wherein the composition further comprises a neutral solid and wherein the neutral solid is a gauze.

51. The kit of paragraph 49, wherein the composition further comprises a neutral gel and wherein the neutral gel is gelatin.

52. A pharmaceutical composition for topically treating a breach or puncture in a vein or artery, comprising:
    a) an effective amount of a vasoconstrictor, wherein the vasoconstrictor does not comprise a poly-β-1→4 N-acetylglucosamine polymer or derivative thereof; and
    b) wherein the vasoconstrictor is formulated into a barrier, membrane, or film.

53. The pharmaceutical composition of paragraph 52, wherein the composition further comprises a coagulant.

54. The pharmaceutical composition of paragraphs 52 or 53, further comprising a neutral liquid, neutral gel or neutral solid.

55. The pharmaceutical composition of paragraph 52, wherein the composition further comprises a neutral solid and wherein the neutral solid is a gauze.

56. A kit comprising in one or more containers a composition comprising:
    a) an effective amount of a vasoconstrictor, wherein the vasoconstrictor does not comprise a poly-β-1→4 N-acetylglucosamine polymer or derivative thereof; and
    b) wherein the vasoconstrictor is formulated into a barrier, membrane, or film,
and instructions for topically treating a breach or puncture in a vein or artery.

57. The kit of paragraph 56, wherein the composition further comprises a coagulant.

58. The kit of paragraph 56, wherein the composition further comprises a neutral liquid, neutral gel or neutral solid.

59. The kit of paragraph 56, wherein the composition further comprises a neutral solid and wherein the neutral solid is a gauze.

60. The kit of paragraph 56, wherein the vasoconstrictor is Adrenaline™ and the composition comprises about 0.00001 mg/kg to about 0.5 mg/kg of patient body weight of Adrenaline™.

61. The kit of paragraph 56, wherein the vasoconstrictor is metaraminol bitartrate and the composition comprises about 0.0005 mg/kg to about 4.5 mg/kg of patient body weight of metaraminol bitartrate.

62. The kit of paragraph 56, wherein the vasoconstrictor is dopamine HCl and the composition comprises about 0.0005 mg/kg to about 10 mg/kg of patient body weight of dopamine HCl.

63. The kit of paragraph 56, wherein the vasoconstrictor is isoproterenol HCl and the composition comprises about 0.0005 mg/kg to about 5 mg/kg of patient body weight of isoproterenol HCl.

64. The kit of paragraph 56, wherein the vasoconstrictor is norepinephrine and the composition comprises about 0.0001 mg/kg to about 0.01 mg/kg of norepinephrine.

65. The kit of paragraph 56, wherein the vasoconstrictor is Serotonin™ and the composition comprises about 0.001 mg/kg to about 0.6 mg/kg of patient body weight of Serotonin™.

66. The kit of paragraph 56, wherein the vasoconstrictor is endothelin and the composition comprises about $4.5 \times 10^{-8}$ mg/kg to about $5.0 \times 10^{-6}$ mg/kg of patient body weight of endothelin.

What is claimed is:

1. A method for treating a puncture in a vein or artery resulting from a cardiac catheterization procedure in a patient, comprising:
   a) applying topically over a catheter exit site on the skin of a patient in need of such treatment a composition comprising an effective amount of one or more vasoconstrictor, wherein the vasoconstrictor does not comprise a poly-β-1→4 N-acetylglucosamine polymer or derivative thereof, and wherein the catheter exit site is contiguous with the catheter puncture in the vein or artery by 1-10 cm; and concurrently
   b) applying compression to the punctured vein or artery.

2. A method for treating a puncture in a femoral artery resulting from a cardiac catheterization procedure in a patient, comprising:
   a) applying topically over a catheter exit site on the skin of a patient in need of such treatment a composition comprising an effective amount of one or more vasoconstrictor, wherein the vasoconstrictor does not comprise a poly-β-1→4 N-acetylglucosamine polymer or derivative thereof, and wherein the catheter exit site is contiguous with the catheter puncture in the femoral artery by 1-10 cm; and concurrently
   b) applying compression to the punctured femoral artery.

3. The method of claim 1 or 2, wherein the vasoconstrictor is endothelin, endothelin-1, epinephrine, adrenaline, metaraminol bitartrate, dopamine HCl, isoproterenol HCl, norepinephrine, phenylephrine, serotonin, thromboxane, norepinephrine, prostaglandin, methergine, oxytocin, isopreland U-46619, papaverine, yohimbine, visnadin, khellin, bebellin, or nicotinate derivatives.

4. The method of claim 1 or 2, wherein the composition further comprises an anti-fungal or antibacterial agent.

5. The method of claim 1 or 2, wherein the composition further comprises collagen.

6. The method of claim 1 or 2, wherein the composition further comprises a pharmaceutical carrier.

7. The method of claim 1 or 2, wherein the composition is formulated as a gel, a solid, a liquid, a sponge, a foam, a spray, an emulsion, a suspension, or a solution.

8. The method of claim 1 or 2, wherein the composition further comprises a neutral liquid, a neutral gel or a neutral solid.

9. The method of claim 8, wherein the composition further comprises a neutral solid and wherein the neutral solid is a gauze.

10. The method of claim 7, wherein the composition is in the form of a coating on a neutral solid.

11. The method of claim 10, wherein the neutral solid is a gauze.

12. The method of claim 1 or 2, wherein the barrier-forming material is a gauze.

13. The method of claim 1 or 2, wherein the composition further comprises one or more coagulant.

14. The method of claim 1 or 2, wherein the patient is a human.

15. The method of claim 1 or 2, wherein the composition applied is a film or a membrane.

16. The method of claim 15, wherein the film or membrane comprises a barrier-forming material.

17. The method of claim 1 or 2, wherein the composition is formulated as a mat, a string, a microbead, a microsphere, or a microfibril.

18. The method of claim 1 or 2, wherein the composition further comprises one or more biodegradable material.

19. The method of claim 18, wherein the biodegradable material is a polyanionic polysaccharide, alginic acid, collagen, a polypeptide, a polyglycolide, a polylactide, a polycaprolactone, dextran and a copolymer of dextran, a polyglycolide, a polylactide, a polydioxanone, a polyestercarbonate, a polyhydroxyalkonate, a polycaprolactone, or a copolymer thereof.

20. The method of claim 1 or 2, further comprising before step (a) the step of administering to the patient an anticoagulant.

21. The method of claim 20, wherein the anticoagulant comprises one or more of coumadin, heparin, nadroparin, aspirin, or a thrombolytic agent.

22. The method of claim 21, wherein the composition further comprises protamine sulfate in an amount effective to neutralize heparin.

23. The method of claim 1, wherein the artery is the femoral, radial, brachial, or axillary artery.

24. The method of claim 1 or 2, wherein the compression is manual compression.

25. The method of claim 1 or 2, wherein the compression is applied to the vein or artery proximal of the puncture or breach.

26. The method of claim 1 or 2, wherein the compression is applied at the site of application of the composition.

27. The method of claim 1 or 2, wherein the compression is applied with a compression bandage.

28. The method of claim 1 or 2, further comprising, repeating step (b).

29. The method of claim 1 or 2, wherein the vein or artery is breached or punctured by a catheter.

30. The method of claim 1 or 2, wherein the skin wound contiguous with the breach or puncture in the vein or artery is 10, 9, 8, 7, 6, 5, or 4 cm from the puncture in the vein or artery.

31. The method of claim 13, wherein the coagulant is alpha-2-antiplasmin, alpha-1-antitrypsin, alpha-2-macroglobulin, aminohexanoic acid, aprotinin, a source of Calcium ions, calcium alginate, calcium-sodium alginate, casein Kinase II, chitin, chitosan, collagen, cyanoacrylates, epsilon-aminocaproic acid, Factor XIII, fibrin, fibrin glue, fibrinogen, fibronectin, gelatin, living platelets, methacrylates, PAI-1, PAI-2, plasmin activator inhibitor, plasminogen, platelet agonists, protamine sulfate, prothrombin, an RGD peptide, sphingosine, a sphingosine derivative, thrombin, thromboplastin, or tranexamic acid.

32. The method of claim 1, wherein the compression is applied for at least one time interval of up to ten minutes.

33. The method of claim 2, wherein the compression is applied for at least one time interval of up to ten minutes.

* * * * *